US007142911B2

(12) United States Patent
Boileau et al.

(10) Patent No.: US 7,142,911 B2
(45) Date of Patent: Nov. 28, 2006

(54) METHOD AND APPARATUS FOR MONITORING DRUG EFFECTS ON CARDIAC ELECTRICAL SIGNALS USING AN IMPLANTABLE CARDIAC STIMULATION DEVICE

(75) Inventors: Peter Boileau, Valencia, CA (US); Janice Barstad, Eden Prairie, MN (US); Gene A. Bornzin, Simi Valley, CA (US); Kerry Bradley, Glendale, CA (US); Eric Falkenberg, Simi Valley, CA (US); Joseph J. Florio, La Canada, CA (US)

(73) Assignee: Pacesetter, Inc., Sylmar, CA (US)

( * ) Notice: Subject to any disclaimer, the term of this patent is extended or adjusted under 35 U.S.C. 154(b) by 487 days.

(21) Appl. No.: 10/608,409

(22) Filed: Jun. 26, 2003

(65) Prior Publication Data

US 2004/0267321 A1    Dec. 30, 2004

(51) Int. Cl.
*A61N 1/365* (2006.01)
*A61N 1/362* (2006.01)

(52) U.S. Cl. .................. 607/3; 607/5; 607/7; 607/8; 607/9; 607/14; 607/17; 600/515; 600/518; 600/508; 600/510; 514/821; 424/9.1; 424/9.2

(58) Field of Classification Search ............ 607/3, 607/5, 7–9, 14, 17, 25–27, 30, 31, 123, 63, 607/22; 600/515, 518, 508, 510; 514/821; 424/9.1, 9.2
See application file for complete search history.

(56) References Cited

U.S. PATENT DOCUMENTS

| 4,399,820 A | 8/1983 | Wirtzfeld et al. ..... 128/419 PG |
| 4,596,255 A | 6/1986 | Snell et al. ................. 128/697 |
| 4,644,954 A | 2/1987 | Wittkampf et al. ... 128/419 PG |
| 4,759,366 A | 7/1988 | Callaghan ............. 128/419 PG |
| 4,791,936 A | 12/1988 | Snell et al. ................. 128/697 |

(Continued)

FOREIGN PATENT DOCUMENTS

WO    WO 01/34088 A2    5/2001

(Continued)

OTHER PUBLICATIONS

Marcus F. I., Opie L. H. *Antiarrhymic Drugs*, Opie L H (Ed) *Drugs for the Heart*, Fourth edition, W B Saunders Company, Philadelphia, 1997, pp. 207-247.

*Primary Examiner*—Robert E. Pezzuto
*Assistant Examiner*—Deborah Malamud

(57) ABSTRACT

An implantable cardiac stimulation device, such as a pacemaker or Implantable Cardioverter Defibrillator, is configured to automatically monitor the effects of antiarrhythmic drugs on cardiac electrical signals within a patient to verify the efficacy of the drugs taken. In one example, an analysis of patient cardiac electrical signals is performed by comparing the cardiac electrical signals with values representative of the effects of different classes of antiarrhythmic drugs. If the implantable device determines that the prescribed antiarrhythmic drugs have not been effective, a warning signal is generated. The warning signal is conveyed directly to the patient via a bedside monitor and to the patient's physician via remote connection to an external programmer device so that both are notified of the drug efficacy problems. Additionally, the implantable device may be configured to automatically adjust pacing and defibrillation control parameters in an attempt to compensate for any lack of efficacy in the drugs. For example, the aggressiveness of overdrive pacing may be increased. Alternatively, a drug pump is controlled to adjust the dosage of antiarrhythmic drugs if an initial dosage is found to be ineffective.

18 Claims, 11 Drawing Sheets

U.S. PATENT DOCUMENTS

| | | | |
|---|---|---|---|
| 4,865,036 A | 9/1989 | Chirife | 128/419 D |
| 5,154,171 A | 10/1992 | Chirife | 128/419 PG |
| 5,405,362 A * | 4/1995 | Kramer et al. | 607/5 |
| 5,466,254 A | 11/1995 | Helland | 607/123 |
| 5,474,574 A * | 12/1995 | Payne et al. | 607/7 |
| 5,605,159 A | 2/1997 | Smith et al. | 128/702 |
| 5,690,682 A | 11/1997 | Buscemi et al. | 607/3 |
| 5,716,382 A | 2/1998 | Snell | 607/30 |
| 5,779,645 A | 7/1998 | Olson et al. | 600/518 |
| 5,817,131 A | 10/1998 | Elsberry et al. | 607/5 |
| 5,824,020 A | 10/1998 | Cooper | 607/17 |
| 5,913,879 A | 6/1999 | Ferek-Petric et al. | 607/14 |
| 5,925,066 A * | 7/1999 | Kroll et al. | 607/3 |
| 5,941,831 A | 8/1999 | Turcott | 600/515 |
| 5,957,957 A | 9/1999 | Sheldon | 607/17 |
| 5,974,341 A | 10/1999 | Er et al. | 607/31 |
| 6,128,534 A | 10/2000 | Park et al. | 607/17 |
| 6,516,219 B1 | 2/2003 | Street | 600/515 |
| 6,941,168 B1 * | 9/2005 | Girouard | 607/3 |
| 2002/0077620 A1 | 6/2002 | Sweeney et al. | 604/502 |
| 2003/0078632 A1 | 4/2003 | Ujhelyi et al. | 607/46 |
| 2003/0144701 A1* | 7/2003 | Mehra et al. | 607/17 |
| 2003/0153951 A1* | 8/2003 | Ideker et al. | 607/3 |
| 2004/0064062 A1* | 4/2004 | Zhou et al. | 600/515 |
| 2005/0033368 A1* | 2/2005 | Fishler et al. | 607/9 |

FOREIGN PATENT DOCUMENTS

| | | |
|---|---|---|
| WO | WO 01/34088 A3 | 5/2001 |
| WO | WO 02/087681 A2 | 11/2002 |

* cited by examiner

METHOD AND APPARATUS FOR MONITORING DRUG EFFECTS ON CARDIAC ELECTRICAL SIGNALS USING AN IMPLANTABLE CARDIAC STIMULATION DEVICE

FIELD OF THE INVENTION

The invention generally relates to implantable cardiac stimulation devices and to external programmer devices for use in connection therewith.

BACKGROUND OF THE INVENTION

An arrhythmia is an abnormal heart rhythm. One example of an arrhythmia is bradycardia wherein the heart beats at an abnormally slow rate or wherein significant pauses occur between consecutive beats. Other examples of arrhythmias include tachyarrhythmias wherein the heart beats at an abnormally fast rate. With atrial tachycardia, the atria of the heart beat abnormally fast. With ventricular tachycardia, the ventricles of the heart beat abnormally fast. Though often unpleasant for the patient, an atrial tachycardia is typically not fatal. However, some tachycardia, particularly ventricular tachycardia, can trigger ventricular fibrillation wherein the heart beats chaotically resulting in little or no net flow of blood from the heart to the brain and other organs. Ventricular fibrillation, if not terminated, is fatal. Hence, it is highly desirable to prevent or terminate arrhythmias, particularly ventricular tachycardia.

Assuming an arrhythmia is symptomatically significant, one or more antiarrhythmic cardioactive drugs may be prescribed to prevent or reduce episodes of the arrhythmia. Exemplary cardioactive drugs include Quinidine, Lidocaine, Sotalol, and Ibutilide. These and other cardioactive drugs are classified in the Vaughn-Williams classification system (Table I) according to the method of action. Class I drugs inhibit sodium ion channels in the cellular membrane. Class II drugs act as beta blockers. Class III drugs inhibit potassium channels. Class IV drugs inhibit calcium channels. Details regarding antiarrhythmic drugs are provided in Marcus F. I., Opie L. H. *Antiarrhythmic Drugs*, in Opie L H (Ed) *Drugs for the Heart*, Fourth edition, W B Saunders Company, Philadelphia, 1997, pp 207–247, which is incorporated by reference herein.

TABLE I

| | |
|---|---|
| Class IA | Procainamide, Quinidine, Disopyramide |
| Class IB | Lidocaine, Mexiletine, Tocainide, Phenytoin |
| Class IC | Flecainide, Propafenone, Moricizine |
| Class II | Acebutalol, Propranolol, Esmolol |
| Class III | Bretylium, Amiodarone, Sotalol, Ibutilide |
| Class IV | Verapamil, Diltiazem, Adenosine |

Although antiarrhythmic drugs have been found to be generally effective when prescribed with the appropriate dosage, it is often difficult for the physician to ensure that the appropriate dosage is actually being taken by the patient. Some patients fail to take the prescribed dosage, either intentionally (because they want to avoid perceived side effects of the drug) or unintentionally (because they simply forget to take the drug or run out of the drug). Even if the prescribed dosage of the drug is properly taken, the patient may become immune to effects of drug with time as a result of electrical changes in the heart, development of a new arrhythmia, a myocardial infarction or other factors. On the other hand, a general improvement in the cardiovascular health of the patient as a result of changes to diet or exercise may result in the prescribed dosage becoming unnecessarily strong. In still other cases, the efficacy of a prescribed drug may be affected by conflicts with other drugs. Accordingly, it may be necessary for the patient to frequently visit the physician so that the physician can evaluate the efficacy of the drug and, if necessary, change the dosage or prescribe new or different drugs. Frequent office visits are expensive and inconvenient. Moreover, even with frequent office visits, the physician cannot be completely assured that the correct dosage is applied at all times between office visits. Hence the patient may not be receiving optimal drug therapy at all times.

Another general technique for preventing or reducing episodes of the arrhythmia is to pace or overdrive pace the heart. An implantable cardiac stimulation device, such as a pacemaker, is implanted within the patient to apply electrical pacing pulses to the heart. For bradycardia, the pacemaker may typically be programmed to pace the heart at a rate of 60 to 80 pulses per minute (ppm) to thereby prevent the heart from beating too slowly and to eliminate any long pauses between heartbeats. To prevent tachyarrhythmias from occurring, the pacemaker can be programmed to overdrive pace the heart at a rate faster than the intrinsic heart rate of the patient. Adjustable parameters of the pacemaker are programmed by the physician in an attempt to provide optimal pacing therapy. If antiarrhythmic drugs are also prescribed, programming typically should take into account the efficacy of the drugs. If the drugs are highly effective, generally non-aggressive pacing therapy may be warranted; whereas if the drugs are not very effective, more aggressive pacing therapy should be employed. Hence, changes in the efficacy of antiarrhythmic drugs or changes in the cardiovascular health of the patient may warrant reprogramming of the pacemaker. Frequent office visits are thus also required to ensure pacemakers are optimally programmed based on the possible changes in the efficacy of the antiarrhythmic drugs or other factors. Even with frequent office visits, the physician cannot be completely assured that the optimal programming is provided at all times between office visits. Hence the patient may not be receiving optimal pacing therapy at all times.

For patients at risk of atrial or ventricular fibrillation, an implantable cardioverter defibrillator (ICD) is implanted, which is a device programmed to detect fibrillation and administer an electrical shock to the heart to terminate fibrillation. For atrial tachycardia or fibrillation, antitachycardia pacing or a defibrillation shock may be delivered. For ventricular fibrillation, a defibrillation shock is delivered. If antiarrhythmic drugs are also used, programming of the ICD should preferably take into account the efficacy of the drugs. For example, if antiarrhythmic drugs are not particularly effective, it may be desirable to program the ICD to charge internal capacitors promptly upon detection of slight changes in certain characteristics of the IEGM (internal electrocardiogram) of the patient that indicate a possible imminent ventricular fibrillation, particularly an increase in RT intervals combined with an increase in heart rate. If, instead, the antiarrhythmic drugs are generally effective, slight changes in those IEGM characteristics may not warrant immediate charging of the capacitors. Hence, as with pacemakers, changes in the efficacy of antiarrhythmic drugs or changes in the general cardiovascular health of the patient may warrant reprogramming of the device and frequent office visits may be required to ensure the ICD is optimally programmed at all times.

Thus significant problems can arise as a result of changes in the administration or efficacy of antiarrhythmic drugs. Accordingly, it would be highly desirable to provide techniques with which an implanted cardiac rhythm management device may measure features of cardiac electrical signals typically affected by cardioactive drugs. Note that, herein, the term "event" refers to P-waves, R-waves, etc.; whereas the term "feature" refers to quantifiable aspects of events, such as duration, slope, and time between events or any quantifiable morphology. Furthermore, it is desirable to provide techniques for automatically verifying the administration of particular antiarrhythmic drugs, monitoring the efficacy of the drugs while the patient is out of the clinic and promptly warning the patient or physician (remotely) of any failure to administer the drugs or any significant change in efficacy of the drugs, thus reducing the need for frequent office visits. It would also be desirable to provide a technique for automatically adjusting dosages of antiarrhythmic drugs based on changes in drug efficacy to thereby ensure the optimal dosage at all times. It would also be desirable to provide a technique for automatically adjusting control parameters of a pacemaker or ICD based on changes in drug efficacy to thereby ensure optimal pacing therapy at all times. For patient with ICDs, it would further be desirable to provide a technique for automatically adjusting defibrillation control parameters based on drug efficacy. It is to these ends that the invention is primarily drawn.

Another area in which the automatic monitoring of the efficacy of antiarrhythmic drugs is highly desirable is in connection with patients receiving antiarrhythmic drugs that prolong RT (or QT) intervals, such as Amiodarone or Sotalol. (Conventionally, "QT" refers to the interval between an intrinsic ventricular depolarization event (QRS complex) and the subsequent repolarization (T-wave) as detected within a surface electrocardiogram (ECG). RT refers to substantially the same interval but as detected within the IEGM. The term "RT interval" will be used herein since the invention relates to the processing of IEGM signals rather than ECG signals.) It is crucial patients receiving such antiarrhythmic drugs remain at rest until the RT intervals have returned to a nominal state. Failure to remain at rest can increase heart rate which, in combination with the increased RT intervals, can trigger serious and potentially fatal arrhythmias, such as torsades de pointes or ventricular fibrillation. Typically, patients are required to remain at rest for one to six hours after the drug is administered. For some patients, the RT intervals return to the nominal state more quickly and further rest is not necessary. For other patients, though, the RT intervals do return to the nominal state within six hours and further rest is mandatory. It would be desirable to provide a technique for automatically monitoring the effect of antiarrhythmic drugs on RT intervals to automatically and promptly determine when the patient can resume normal activities. Aspects of the invention are directed to this end as well.

SUMMARY

In accordance with one illustrative embodiment, a technique is provided for automatically monitoring the effects of antiarrhythmic drugs within a patient using an implantable cardiac stimulation device to, for example, verify that antiarrhythmic drugs are being taken by the patient, to determine the classes of the antiarrhythmic drugs being taken, and to verify the efficacy of the drugs.

In one embodiment, the implantable cardiac stimulation device is configured to analyze patient cardiac electrical signals to detect the effects, if any, on the cardiac electrical signals caused by prescribed antiarrhythmic drugs and to then control device operations based on the results of the analysis of the patient cardiac electrical signals. For example, the stimulation device may increase the aggressiveness of overdrive pacing if prescribed antiarrhythmic drugs have been found to be ineffective. The stimulation device may alternatively control a drug pump to increase the dosage of antiarrhythmic drugs if an initial dosage is found to be ineffective. If the stimulation device includes an ICD, defibrillation capacitors may be automatically charged if antiarrhythmic drugs have been found to be ineffective in reducing RT intervals and the patient heart rate begins to increase significantly (resulting in a risk of torsades de points). For patients receiving antiarrhythmic drugs that prolong RT interval, the implantable cardiac stimulation device is preferably configured to track RT intervals and to generate a notification signal when RT intervals have returned to a nominal state following receipt of the antiarrhythmic drugs to help reduce risk or torsades de points. For other antiarrhythmic drugs, the stimulation device may simply generate a warning signal if the analysis of patient cardiac electrical signals reveals that prescribed antiarrhythmic drugs have become ineffective. The warning signal may be conveyed directly to the patient via a bedside monitor or to the physician via remote connection to a programmer device. In this manner, if the patient forgets to take prescribed drugs, the patient can be automatically reminded. If the patient becomes immune to prescribed drugs, the physician can be automatically notified so that an office visit can be arranged, if necessary, to review stored diagnostic information and prescribe new or different antiarrhythmic drugs.

In one example, the analysis of patient cardiac electrical signals is performed by inputting values representative of the expected changes to cardiac electrical signals caused by different classes of antiarrhythmic drugs and then comparing actual changes detected in the patient's cardiac electrical signals with the expected changes to verify drug efficacy. In another example, the analysis of patient cardiac electrical signals is performed by inputting templates representative of the expected shapes of cardiac signal features resulting from the different classes of antiarrhythmic drugs and then comparing actual portions of the patient cardiac electrical signals with the templates to verify drug efficacy. In general, each class of antiarrhythmic drugs has a unique effect on cardiac electrical signals that can be represented either with trend tables or feature templates. The more effective the drug, the more significant the effect on the cardiac electrical signals. Hence, a comparison of patient cardiac electrical signals with the trend tables or templates can reveal the particular class of antiarrhythmic drug taken by the patient and its efficacy. Ideally, comparisons are performed based on patient signals detected only while the patient is asleep to maximize comparison reliability.

Thus, a pacemaker, ICD or other implantable device is configured to automatically verify the administration of antiarrhythmic drugs and to monitor the drugs' efficacy, thereby eliminating the need for frequent office visits. Minor changes in the efficacy of the drugs or in the general cardiovascular health of the patient can be automatically compensated via internal adjustment of pacing control parameters or administration of an additional dosage of drugs via a drug pump. Hence, optimal dosages and optimal pacing control parameters may be employed at all times without the need for frequent office visits. Indeed, an office visit may only be necessary if changes in the efficacy of the drugs or in the general cardiovascular health are so significant that the changes cannot be automatically compensated.

System and method embodiments of the invention are provided herein. Embodiments wherein the analysis of the patient cardiac signal is preformed by an external device, such as a device programmer or bedside monitor, are also provided.

BRIEF DESCRIPTION OF THE DRAWINGS

Further features and advantages of the present invention may be more readily understood by reference to the following description taken in conjunction with the accompanying drawings, in which.

DETAILED DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Overview of Implantable Device

Figure 1:
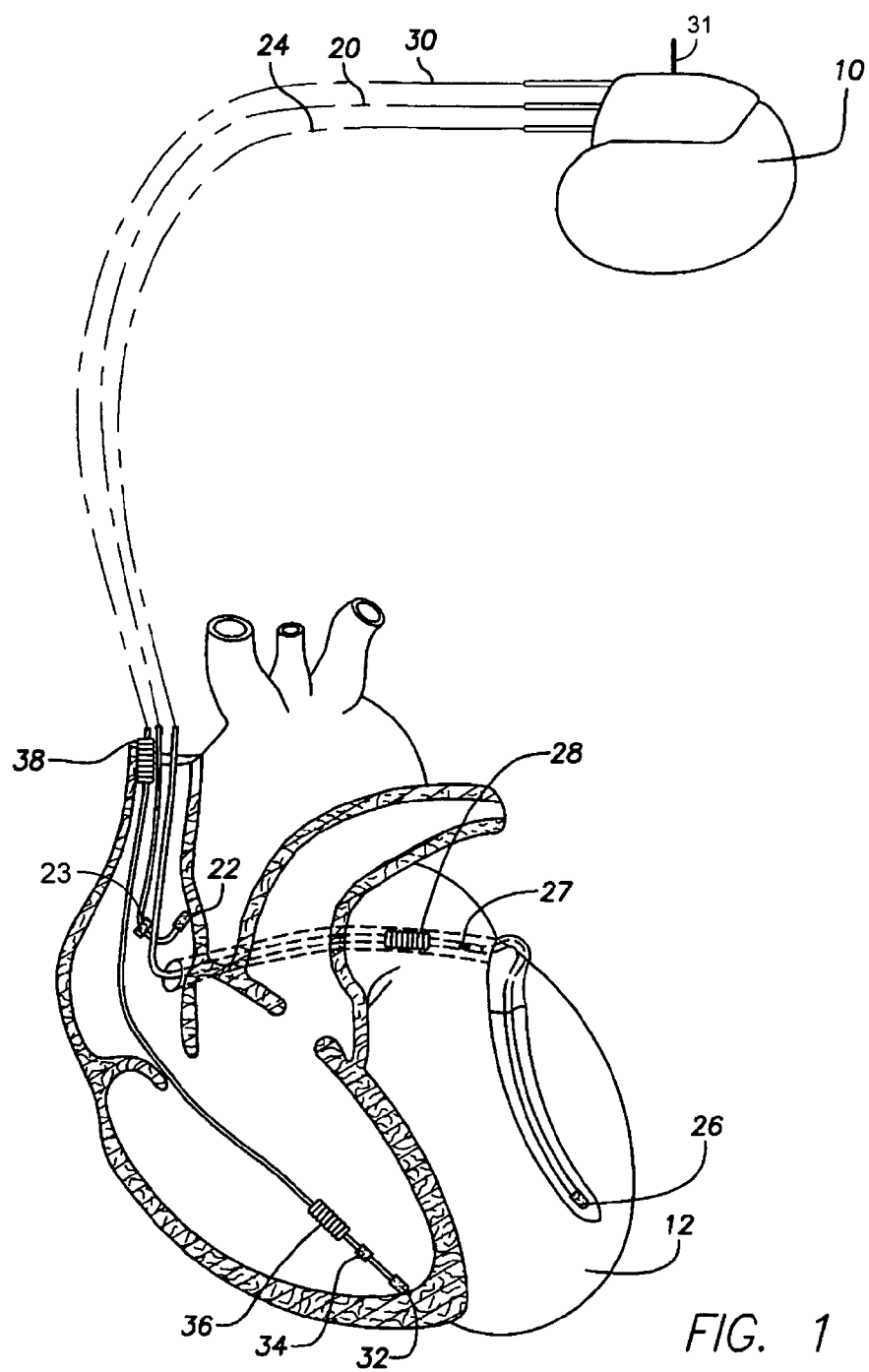
FIG. 1 is a simplified diagram illustrating an implantable stimulation device for delivering multi-chamber stimulation and shock therapy to the heart of a patient.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac electrical signals and to provide right atrial chamber stimulation therapy, the stimulation device 10 is coupled to an implantable right atrial lead 20 having at least an atrial tip electrode 22, which typically is implanted in the patient's right atrial appendage and an atrial ring electrode 23.

To sense left atrial and ventricular cardiac electrical signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac electrical signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac electrical signals, and delivering stimulation in the form of pacing and shock therapy to the right ventricle.

Figure 2:
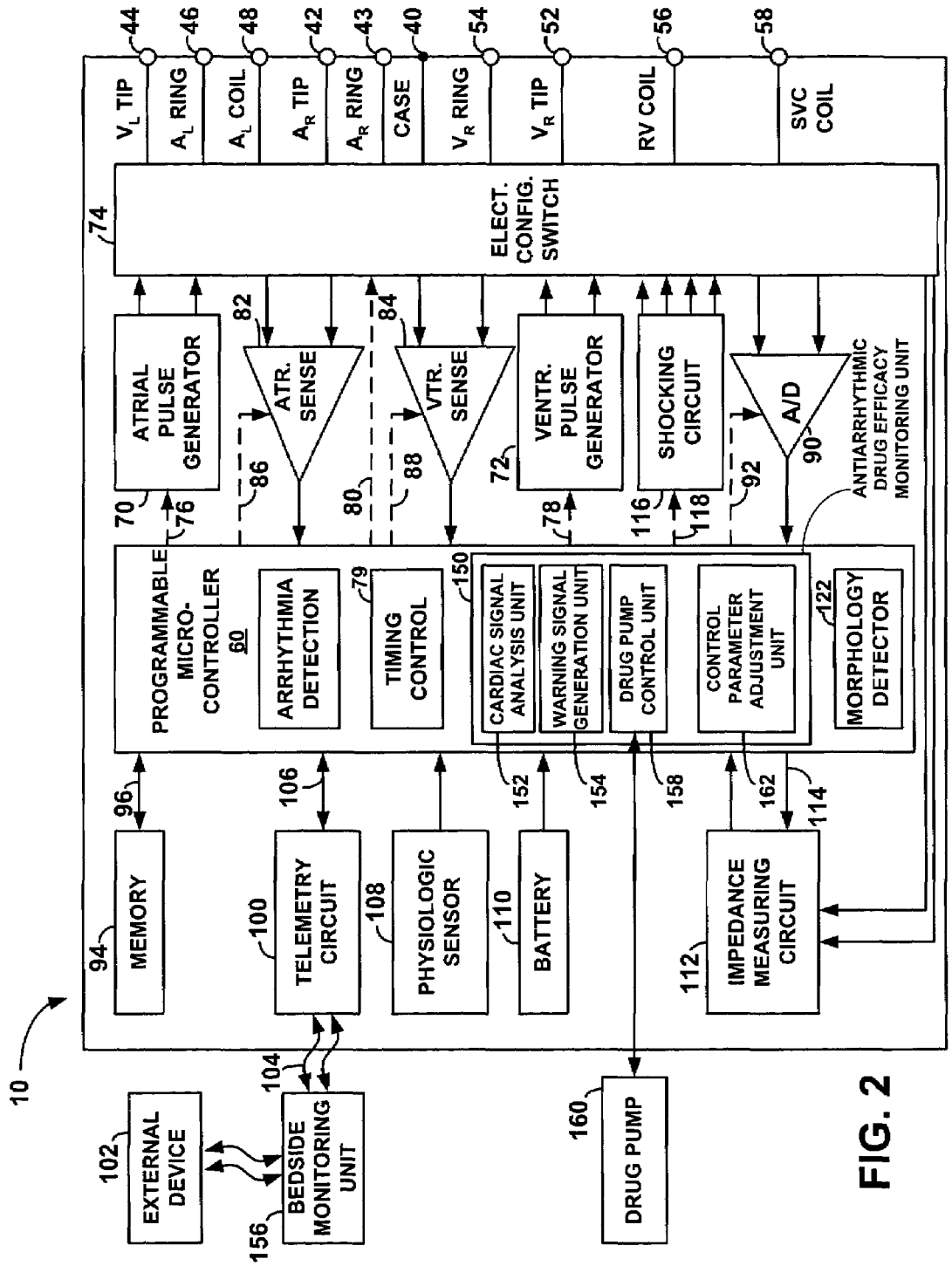
FIG. 2 is a functional block diagram illustrating internal components of the stimulation device of FIG. 1, which includes an antiarrhythmic drug efficacy monitoring unit configured to automatically monitor the efficacy of antiarrhythmic drugs taken by the patient.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar"

modes. The housing 40 may further be used as a return electrode alone or in combination with one or more of the coil electrodes, 28, 36 and 38, for shocking purposes. The housing 40 further includes a connector (not shown) having a plurality of terminals, 42, 43, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22. The connector also includes a right atrial ring terminal ($A_R$ RING) 43 adapted for connection to the atrial ring electrode 23. To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60, which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art. Microcontroller 60 controls the operation of the stimulation device using various control parameters received from the external programmer.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac electrical signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Morphology detection and analysis is performed by morphology detector 122.

Cardiac electrical signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac electrical signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. A feature of the present invention is the ability to sense and store a relatively large amount of data (e.g., from the data acquisition system 90), which data may then be used for subsequent analysis to guide the programming of the device.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. Signals are either transmitted directly between the telemetry circuit and the external device or, as shown, are routed through a bedside monitoring unit 156. External device 102 and bedside monitor 156 are described in greater detail below.

The stimulation device additionally includes a battery 110 that provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Stimulation device 10 further includes one or more sensors 108, commonly referred to as "rate-responsive" sensors because they are typically used to adjust pacing stimulation rate according to the exercise state of the patient. However, sensor 108 may further be used to detect changes in cardiac output, changes in the physiological condition of the heart, or diurnal changes in activity (e.g., detecting sleep and wake states). Microcontroller 60 responds by adjusting the various pacing parameters (such as rate, AV Delay, V—V Delay, etc.) at which the atrial and ventricular pulse generators, 70 and 72, generate stimulation pulses. While shown as being included within the stimulation device 10, it is to be understood that sensors 108 may also be external to the stimulation device 10, yet still be implanted within or carried by the patient.

Examples of sensors include: minute ventilation sensors (also known as minute volume sensors) for detecting the total volume of air moved in and out of the lungs in one minute; orthostatic sensors for detecting the physical inclination of the patient; activity variance sensors for detecting a degree of physical activity of the patient; vasovagal syncope sensors for detecting whether the patient is prone to an episode of vasovagal syncope; paced depolarization integral (PDI) sensors (also known as ventricular gradient sensors) for calculating the integral of a paced R-wave; RT interval sensors for detecting the time between ventricular polarization (R-wave) and ventricular re-polarization (T-wave); temperature sensors; oxygen blood saturation sensors; and pre-ejection period (PEP) sensors for detecting the time interval between the onset of ventricular activation (i.e. the onset of an R-wave) and the onset of ventricular ejection (i.e. the opening of the aortic and pulmonic valves).

For a description of a minute ventilation sensors, see U.S. Pat. No. 5,824,020 to Cooper. For a description of an orthostatic sensor, see U.S. Pat. No. 5,957,957 to Sheldon. For a description of an activity variance sensor, see U.S. Pat, No. 6,128,534 to Park et al. For a description of a vasovagal syncope sensor, see U.S. Pat. No. 5,913,879 to Ferek-Petric, et al. For a description of PDI, also known as the ventricular depolarization gradient, see U.S. Pat. No. 4,759,366, to Callaghan. For a description of RT interval, also known as the stimulus-to-evoked T-wave, see U.S. Pat. No. 4,644,954, to Wittkampf et al. For a description of oxygen saturation, see U.S. Pat. No. 4,399,820, to Wirtzfeld et al. For descriptions of pre-ejection period and ejection fraction sensors, see U.S. Pat. Nos. 4,865,036 and 5,154,171, both to Chirife. Each of the aforementioned patents is incorporated herein by reference.

Microcontroller 60 also includes an antiarrhythmic drug efficacy monitoring unit 150 for automatically monitoring the efficacy of antiarrhythmic drugs prescribed to the patient. Monitoring unit 150 includes a cardiac signal analysis unit 152 for analyzing the patient cardiac signal to verify the efficacy of the prescribed drugs and a warning signal generation unit 154 for generating a warning signal for transmitting to a bedside monitoring unit 156 for alerting the patient to possible drug efficacy problems. As will be explained below, the warning signal may also be forwarded from the bedside monitor to a central programmer device, such as external device 102. Monitoring unit 150 also includes a drug pump control unit 158 for automatically controlling an optional implantable drug pump 160 to compensate, if necessary, for drug efficacy problems. For example, if an initial dosage of an antiarrhythmic drug is not adequately effective, the drug pump may be controlled to increase the dosage. Finally, monitoring unit 150 also includes a control parameter adjustment unit 162 for automatically adjusting pacing control parameters used by the implanted device to compensate for drug efficacy problems. For example, if the prescribed antiarrhythmic drug is not adequately effective, overdrive pacing control parameters can be adjusted to increase the aggressiveness of overdrive pacing. The operation of antiarrhythmic drug efficacy monitoring unit 150 and its internal components will be described in greater detail below with reference to FIGS. 5–12. In an alternative embodiment, analysis of the patient cardiac signal is performed by the external programmer 102 and any adjustments to the pacing control parameters or to the optional drug pump are controlled by the external programmer. In the alternative embodiment, monitoring unit 150 is not provided within the implanted device. Rather a similar monitoring unit is provided within the external programmer.

Overview of External Programmer

Figure 3:
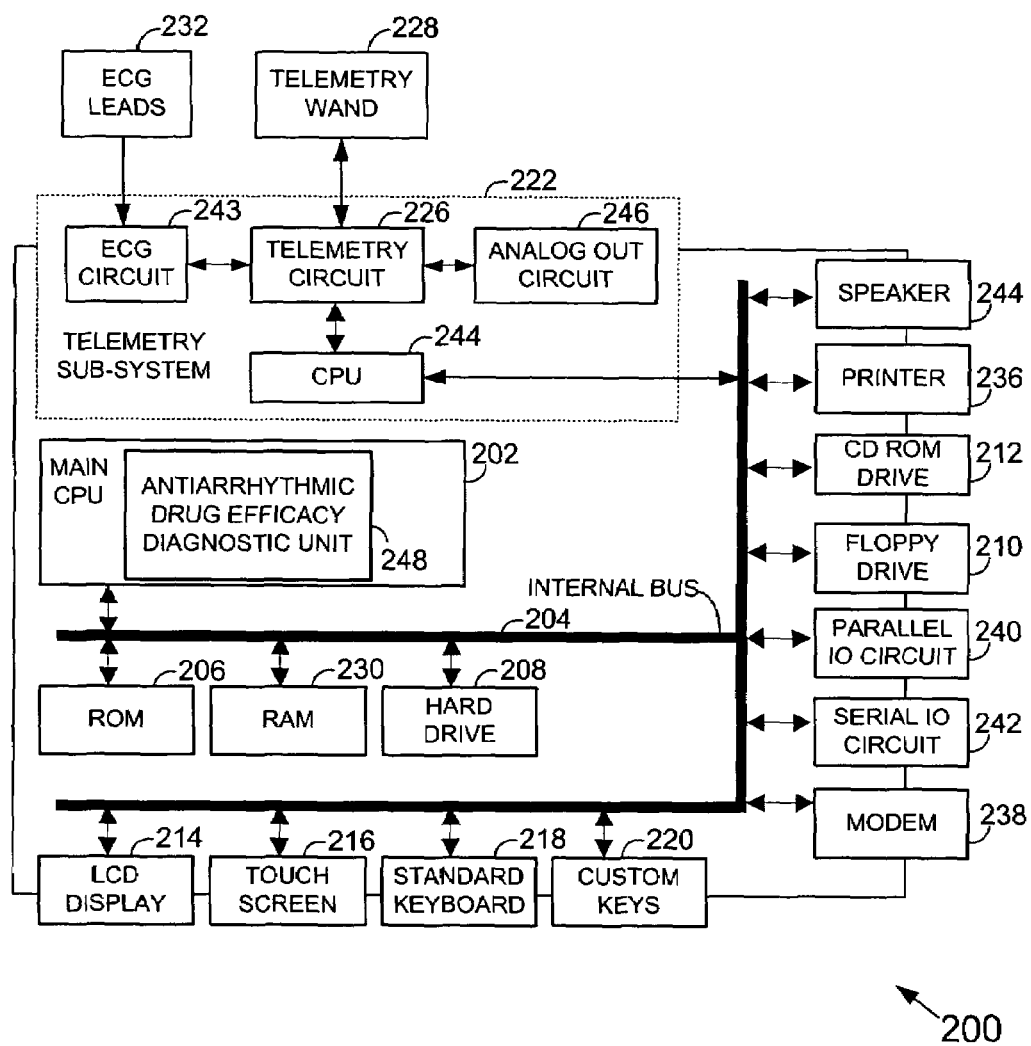
FIG. 3 is a functional block diagram illustrating components of a programmer for use in programming the implantable device of FIG. 2.

FIG. 3 illustrates pertinent components of an external programmer for use in programming an implantable cardiac stimulation device such as a pacemaker or ICD. Briefly, the programmer permits a physician or other user to program the operation of the implanted device and to retrieve and display information received from the implanted device such as IEGM data and device diagnostic data. Additionally, the external programmer receives and displays ECG data from separate external ECG leads that may be attached to the patient. Depending upon the specific programming of the external programmer, programmer 102 may also be capable of processing and analyzing data received from the implanted device and from the ECG leads to, for example, render preliminary diagnosis as to medical conditions of the patient or to the operations of the implanted device.

Now, considering the components of programmer 102, operations of the programmer are controlled by a CPU 202, which may be a generally programmable microprocessor or microcontroller or may be a dedicated processing device such as an application specific integrated circuit (ASIC) or the like. Software instructions to be performed by the CPU are accessed via an internal bus 204 from a read only memory (ROM) 206 and random access memory 230. Additional software may be accessed from a hard drive 208, floppy drive 210, and CD ROM drive 212, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 214 or other suitable computer display device. To this end, the CPU may, for example, display a menu of specific programming parameters of the implanted device to be programmed or may display a menu of types of diagnostic data to be retrieved and displayed. In response thereto, the physician enters various commands via either a touch screen 216 overlaid on the LCD display or through a standard keyboard 218 supplemented by additional custom keys 220, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Typically, the physician initially controls the programmer 102 to retrieve data stored within the implanted cardiac stimulation device and to also retrieve ECG data from ECG leads, if any, coupled to the patient. To this end, CPU 202 transmits appropriate signals to a telemetry subsystem 222, which provides components for directly interfacing with the implanted device, and the ECG leads. Telemetry subsystem 222 includes its own separate CPU 224 for coordinating the operations of the telemetry subsystem. Main CPU 202 of programmer communicates with telemetry subsystem CPU 224 via internal bus 204. Telemetry subsystem additionally includes a telemetry circuit 226 connected to a telemetry wand 228, which, in turn, receives and transmits signals electromagnetically from a telemetry unit of the implanted device. The telemetry wand is placed over the chest of the patient in the vicinity of the implanted device to permit reliable transmission of data between the telemetry wand and the implanted device. Typically, at the beginning of the programming session, the external programming device controls the implanted device via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the implanted device is stored by external programmer 102 either within a random access memory (RAM) 230, hard drive 208 or within a floppy diskette placed within floppy drive 210. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted device is transferred to programmer 102, the implanted device may be further controlled to transmit additional data in real time as it is detected by the implanted device, such as additional IEGM data, lead impedance data, and the like. Additionally, or in the alternative, telemetry subsystem 222 receives ECG signals from ECG leads 232 via an ECG processing circuit 234. As with data retrieved from the implanted device itself, signals received from the ECG leads are stored within one or more of the storage devices of the external programmer. Typically, ECG leads output analog electrical signals representative of the ECG. Accordingly, ECG circuit 234 includes analog to digital conversion circuitry for converting the signals to digital data appropriate for further processing within programmer. Depending upon the implementation, the ECG circuit may be configured to convert the analog signals into event record data for ease of processing along with the event record data retrieved from the implanted device. Typically, signals received from the ECG leads are received and processed in real time. See U.S. Pat. Nos. 4,596,255 and 4,791,936, by Snell et al., both entitled "Apparatus For Interpreting And Displaying Cardiac Events Of A Heart Connected To A Cardiac Pacing Means".

Thus the programmer receives data both from the implanted device and from the external ECG leads. Data retrieved from the implanted device includes parameters representative of the current programming state of the implanted device. Under the control of the physician, the external programmer displays the current programming parameters and permits the physician to reprogram the parameters. To this end, the physician enters appropriate commands via any of the aforementioned input devices and, under control of CPU 202, the programming commands are converted to specific programming parameters for transmission to the implanted device via telemetry wand 228 to thereby reprogram the implanted device. Techniques for programming an implanted cardiac stimulation device may be found in U.S. Pat. No. 5,716,382 entitled "Programmer For An Implantable Cardiac Stimulating Device". Prior to reprogramming specific parameters, the physician may control the external programmer to display any or all of the data retrieved from the implanted device or from the ECG leads, including displays of ECGs, IEGMs, and statistical patient information. Further information pertaining to the types of information which may be displayed using programmer may be found in U.S. Pat. No. 5,974,341 entitled "Method And Apparatus For Detecting And Displaying Diagnostic Information In Conjunction With Intracardiac Electrograms And Surface Electrocardiograms". Any or all of the information displayed by programmer may also be printed using a printer 236.

Programmer 102 also includes a modem 238 to permit direct transmission of data to other programmers or to a beside monitor via the public switched telephone network (PSTN) or other interconnection line, such as a T1 line or fiber optic cable. Depending upon the implementation, the modem may be connected directly to internal bus 204 may be connected to the internal bus via either a parallel port 240 or a serial port 242. Other peripheral devices may be connected to the external programmer via parallel port 240 or a serial port 242 as well. Although one of each is shown, a plurality of input output (IO) ports may be provided.

A speaker 244 is included for providing audible tones to the user, such as a warning beep in the event improper input is provided by the physician. Telemetry subsystem 222 additionally includes an analog output circuit 246 for controlling the transmission of analog output signals, such as IEGM signals output to an ECG machine or chart recorder.

With the programmer configured as shown, a physician or other user operating the external programmer is capable of retrieving, processing and displaying a wide range of information received from the ECG leads or from the implanted device and to reprogram the implanted device if needed.

Additionally, CPU 202 includes an antiarrhythmic drug efficacy diagnostic unit 248 configured for displaying drug efficacy warning signals and diagnostic information generated by the drug efficacy monitoring unit of the implanted device (unit 150 of FIG. 2) and forwarded to the external programmer via the bedside monitor (unit 156 of FIG. 2). The warning signals alert the physician that there may be drug efficacy problems within the patient and the diagnostic information allows the physician to review drug efficacy data to determine the nature and extend of the drug efficacy problems. Alternatively, rather than configuring the implanted device to analyze patient cardiac electrical signals to verify drug efficacy, the implanted device merely transmits the patient cardiac electrical signals to the external programmer (via the bedside monitor) and the external programmer instead performs the actual drug efficacy analysis. In that embodiment, the CPU of the external programmer is preferably provided with the antiarrhythmic drug efficacy monitoring unit summarized above including its various components such as the cardiac signal analysis unit and control parameter adjustment unit. Depending upon its programming, the external programmer then generates control signals for adjusting the implanted drug pump or for adjusting the pacing control parameters of the implanted stimulation device. The control signals, subject to review by the physician, are then routed through the modem to the bedside monitor and onto the implanted device. The operation of drug efficacy diagnostic unit 248 will be described in greater detail below with reference to FIGS. 5–12.

Note that the descriptions provided herein with respect to FIG. 3 are provide an overview of the operation of programmer and are not intended to describe in detail each and every feature of the hardware and software of the device and is not intended to provide an exhaustive list of the functions performed by the device.

Overview of Bedside Monitoring Network

Figure 4:
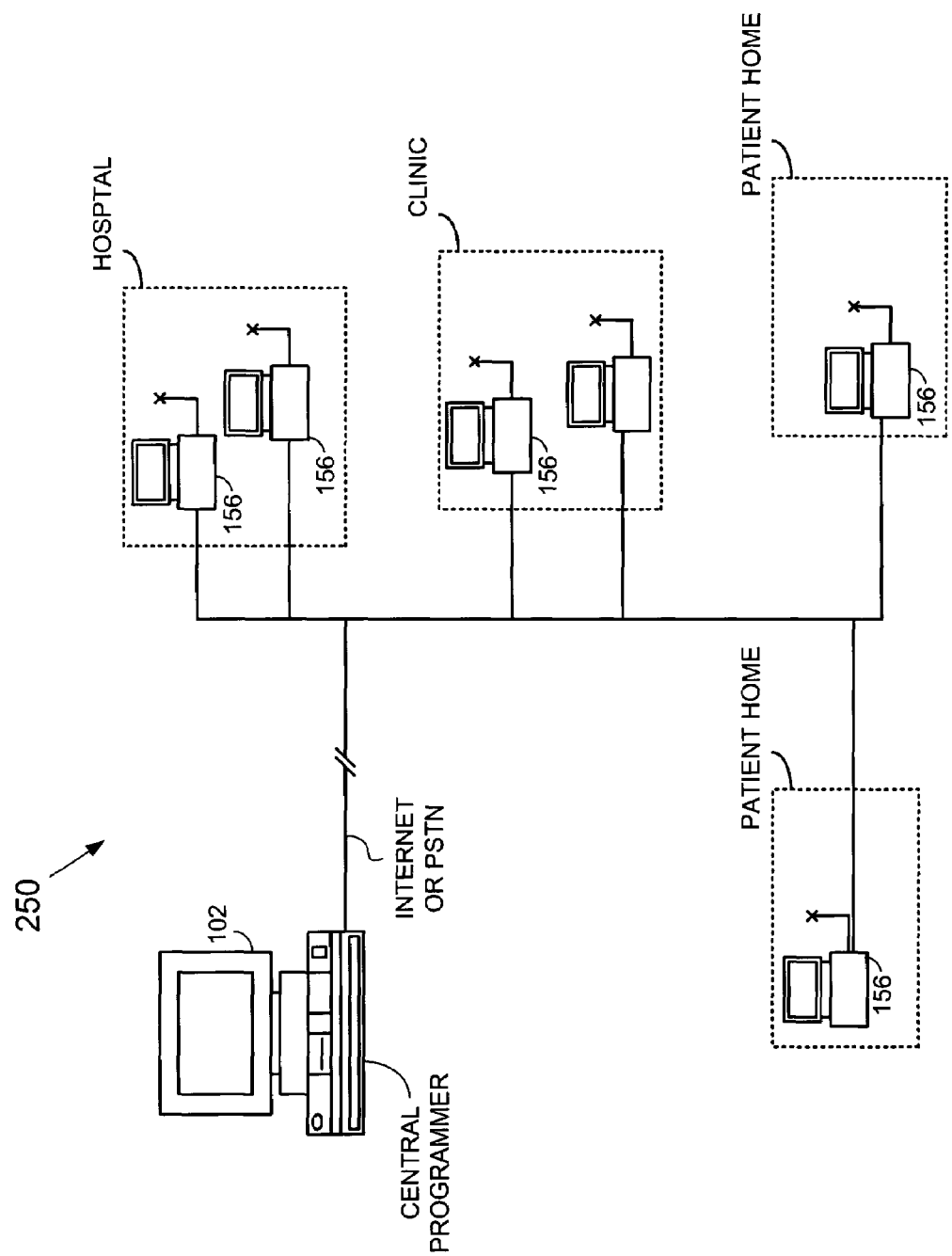
FIG. 4 is a system diagram illustrating a network of bedside monitors for use in relaying drug efficacy information received from individual implantable devices to the programmer of FIG. 3.

FIG. 4 illustrates a bedside monitoring system 250 having individual bedside monitors 156 for displaying drug efficacy warnings received from the implanted device of FIG. 2 directly to the patient and for forwarding the warnings and additional drug efficacy diagnostic information to a central device programmer, such as programmer 102 of FIG. 3, for review by a physician. As noted, the antiarrhythmic drug efficacy monitoring unit provided within each implanted device operates to verify the efficacy of antiarrhythmic drugs prescribed to the patient and to generate warning signals, when warranted, for transmission to a bedside monitor. Warning signals received by the bedside monitor are displayed to the patient to thereby directly alert the patient of any drug efficacy problems. Audible alerts may be provided along with textual displays. Depending upon the configuration of the bedside monitor, specific textual displays may be generated for describing particular warnings. Some exemplary textual warnings are as follows:

Warning—The correct dosage of following prescribed drug has not been taken: Procainamide. If you have forgotten to take the prescribed drug, please remember to do so.

Warning—The correct dosage of following prescribed drug has not been taken: Procainamide. It appears that a different drug has instead been taken. Please contact your physician immediately.

Warning—The following prescribed drug is not as effective as expected: Procainamide. Please contact your physician immediately.

Warning—The following prescribed drug is having a stronger effect than expected: Procainamide. Please contact your physician immediately.

Preferably, confirmation messages are displayed if the correct drug has been taken and is effective. If neither a confirmation message nor a warning message is displayed, the patient is thereby alerted that the bedside monitoring system is not functioning properly and should contact the physician.

The bedside monitors (also referred to herein as remote telemetry units) are preferably provided only with hardware and software sufficient to 1) receive drug efficacy warnings and diagnostic information from an implanted device, 2) display warnings and confirmation messages to the patient, and 3) relay the warnings, confirmation messages and diagnostic information to the central programmer. However, if the external programmer is configured to generate drug pump control signals and pacing control signals for remotely reprogramming the implanted device via the bedside monitor, the bedside monitor must include components for relaying the programming signals to the implanted device.

In any case, the central programmer is installed within a central data collection center or within a physician office, such as the office of a cardiologist supervising the programming of implanted devices within numerous patients. Preferably, each patient having an implanted device with an antiarrhythmic drug efficacy monitoring unit is provided with a bedside monitor. Additionally, as shown, bedside monitors are provided in clinics, hospitals, and the like.

In the specific implementation of FIG. 4, the bedside monitors communicate with the central programmer via the public switched telephone network (PSTN) or other land line communication link, such as T1 line, ISDN line, or the like. Alternatively, individual bedside monitors may be provided with wireless communication devices to permit the bedside monitor to communicate with the central programmer via satellite-based wireless communication systems or cellular telephone systems or the like. In still other implementations, the individual telemetry units communicate with the central programmer via the Internet or other interconnected computer network.

Further information regarding distributed networks of remote telemetry units for use with individual patients may be found in: U.S. patent application Ser. No. 09/823,374, "System And Method For Remote Programming Of Implantable Cardiac Stimulation Devices", filed Mar. 29, 2001, which is assigned to the assignee of rights to the present application and is incorporated by reference herein.

Automatic Monitoring of Drug Efficacy

Figure 5:
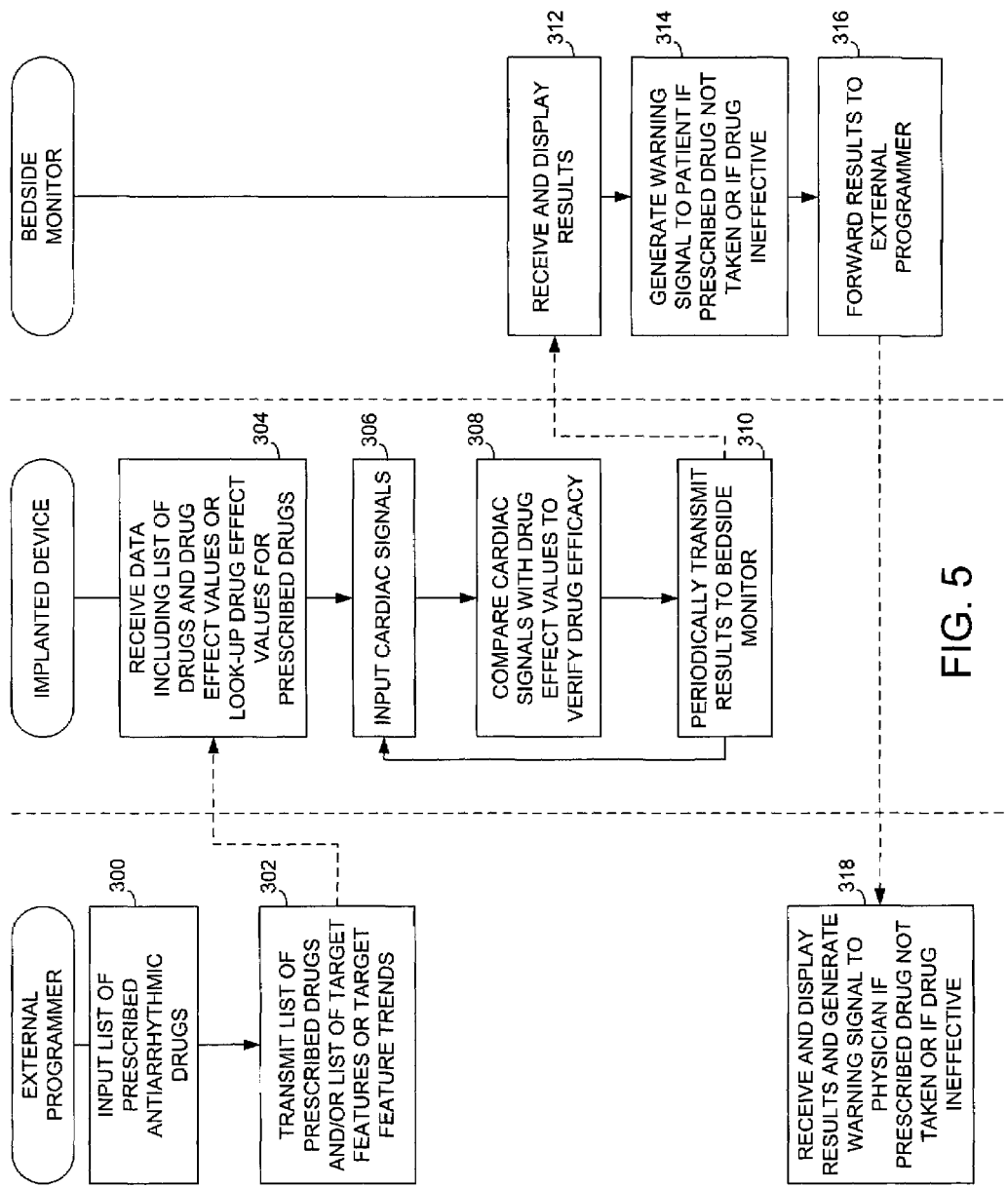
FIG. 5 is a flow chart illustrating, at a high level, an first exemplary method for automatically monitoring drug efficacy, which employs the implantable device of FIG. 2, the external programmer of FIG. 3 and one of the bedside monitoring units of FIG. 4 and wherein warning signals are generated if adequate drug efficacy is not maintained.

The flow chart of FIG. 5 illustrates a method for monitoring drug efficacy within a patient receiving antiarrhythmic drugs using an implantable cardiac pacing device. In the flow chart of FIG. 5, and in other flow charts provided herein, various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein. In the flow chart of FIG. 5, operations performed by the implantable device of FIG. 2 are shown in the middle, operations performed by the external programmer of FIG. 3 are shown on the left, and operations performed by the bedside monitor of FIG. 4 are shown in the right.

Briefly, the method of FIG. 5 operates to 1) verify that prescribed antiarrhythmic drugs are properly taken by a patient, 2) verify the efficacy of the drugs, and 3) generate warning signals if warranted. Techniques for automatically controlling an implanted drug pump or for automatically adjusting pacing control parameters are described below with reference to FIGS. 11 and 12.

Initially, at step 300, during an office visit, the physician enters the names of all antiarrhythmic drugs prescribed to the patient into the external programmer. The list of prescribed drugs is transmitted to the implantable device implanted within the patient at step 302 for storage therein. Alternatively, or additionally, lists of target features or target feature trends may be transmitted. Although not shown in FIG. 5, numerous programming control parameters may also be entered into the external programmer by the physician and transmitted to the implanted device for programming various operations of the device. Examples include control parameters for setting the pacing mode of the device or for controlling the aggressiveness of overdrive pacing (assuming the device if configured to performed overdrive pacing). Typically, the various control parameters are selected by the physician in part based on the assumption that the prescribed antiarrhythmic drugs will in fact be taken by the patient and will be reasonably effective. Accordingly, the aforementioned warning signals are generated if the implanted device detects that either the drugs are not being taken by the patient or are ineffective.

Upon receipt of data transmitted from the external programmer, the implanted device, at step 304, accesses a drug effect table to retrieve values representative of the effects of the prescribed drugs on patient cardiac electrical signals, particularly the, shape and timing (i.e. appropriate delay or interval) of P-waves, R-waves, T-waves, atrial evoked responses (AERs) and ventricular evoked responses (VERs). Alternatively, drug effect table values may be received from the external programmer. In any case, the table groups drugs according to the Vaughn-Williams classification system and provides a single set of drug effect values for each class of drugs. Alternatively, separate sets of values may be provided for individual drugs within each class. However, in general, all drugs within a given class have the same effects on patient cardiac electrical signals and so a single set of values per drug class is sufficient. The drug effect values are described in further detail below with reference to TABLE II. Note that the Vaughn-Williams classification scheme used herein is based upon theoretically distinct mechanisms of drug action. Some of these mechanisms have predictable effects on the electrogram. It is from these effects that the class of drug taken by a patient can be inferred. However, any given drug is likely in reality to exhibit several mechanisms of action, each to varying degrees. Hence, in some cases, the techniques of the invention operate to determine the most likely class of drug rather than to conclusively determine the specific drug class.

Beginning at step 306, the implanted device begins detecting patient cardiac electrical signals, i.e. IEGM signals (or accesses feature data already stored, such as feature history data or feature averages.) Some features, for example the R-wave duration, may be more effectively measured using a far-field sensing configuration. This may be achieved by the cardiac signal analysis unit (unit 152 of FIG. 2) directing the electronic switch configuration unit (unit 74 of FIG. 2) via the control path (path 80 of FIG. 2) to select, for example, an $A_R$ Ring-Case configuration while measuring the R-wave duration. At step 308, the antiarrhythmic drug efficacy monitoring unit (unit 150 of FIG. 2) identifies individual features of the IEGM signals, that is the shape, duration and relative spacing of P-waves, R-waves, and T-waves, and compares the features with corresponding features in the drug effect values to verify that the patient cardiac electrical signals exhibit the effects expected for the prescribed drugs. If the patient cardiac electrical signals do not exhibit the effects of any of the classes of prescribed drugs, the antiarrhythmic drug efficacy monitoring unit stores diagnostic information indicating that the patient has probably not taken any of the prescribed drugs. If the patient cardiac electrical signals exhibit the effects of a different class of drug than prescribed, the antiarrhythmic drug efficacy monitoring unit stores diagnostic information indicating that the patient has probably taken the wrong drug (perhaps as a result of failing to switch from a previously prescribed drug to a newly prescribed drug). If the patient cardiac electrical signals exhibit the effects of the prescribed class of drug but the effects are less than expected, the antiarrhythmic drug efficacy monitoring unit stores diagnostic information indicating a possible inefficacy in the drug (perhaps as a result of a developed immunity to the drug or an adverse drug interaction). If the patient cardiac electrical signals exhibit the effects of the prescribed class of drug but the effects are greater than expected, the antiarrhythmic drug efficacy monitoring unit stores diagnostic information indicating the enhanced efficacy (perhaps resulting from an improvement in the cardiovascular condition of the patient).

Also, at step 308, diagnostic data from various physiologic sensors, such as activity, blood pressure, blood oxygen, minute ventilation or impedance sensors, may be collected and stored. The diagnostic information developed at step 308 is time-stamped and stored, then processing returns to step 306 wherein additional IEGM signals are analyzed by the antiarrhythmic drug efficacy monitoring unit and additional diagnostic information is developed. Periodically, the diagnostic information is averaged and, if the averaged data indicates possible problems with prescription drug compliance or drug efficacy, a warning signal is transmitted at step 310 to the bedside monitor. Moving averages may be employed. Preferably, a sufficient amount of data is processed to warrant a reliable conclusion before warning signals are generated. Data from the physiological sensors may be use to corroborate the drug efficacy conclusions. As one example, a RT (or QT) interval sensor may be used to corroborate a determination of the efficacy of drugs affecting the RT interval.

In one embodiment, patient cardiac electrical signals are analyzed only while the patient is asleep (as detected via activity sensors) and warning signals are generated only if several nights worth of diagnostic data confirms that the patient has failed to take the prescribed drug or that the prescribed drug is not achieving the expected level of efficacy. Alternatively, analysis can be triggered at a particular time of day (e.g. 3:00 am) or can be triggered in whole or in part based on some other qualifier such as a pre-programmed Rest Rate coming into effect, the output of a Circadian Base Rate algorithm crossing a predetermined threshold, or a Sensor Indicated Rate crossing a predetermined threshold. Alternately, the physician may initiate analysis manually via telemetry. Once analysis has commenced, rather than waiting for particular events to occur, such as AERs or VERs, the monitoring unit may be programmed to trigger such events so as to ensure an adequate number of occurrences of the events for reliable drug efficacy analysis.

In any case, once a warning signal is received by the bedside monitor at step 312, the monitor generates a warning at step 314 to the patient, such as the warnings listed above. Assuming the bedside monitor is connected to the physician's external programmer (as with the system of FIG. 4), all warning signals and confirmation signals are directly forwarded from the bedside monitor to the programmer to alert the physician. Hence, the patient need not inform the physician of drug efficacy concerns. Also, preferably, if drug efficacy problems are detected, the implanted device transmits the diagnostic data derived at step 308 (including exemplary IEGM signals) to the bedside monitor for forwarding to the programmer allowing the physician to directly access and review the data. In this manner, the physician can independently corroborate drug efficacy conclusions drawn by the antiarrhythmic drug efficacy monitoring unit.

For the specific case of antiarrhythmic drugs that tend to significantly prolong RT intervals resulting in risk of torsades de pointes, such as Quinidine or Sotalol, the monitoring unit can be programmed to generate a notification signal once the RT interval has returned to nominal. As noted above, it is crucial that patients receiving such drugs remain at rest until the RT intervals have returned to a nominal state. Failure to remain at rest can increase heart rate which, in combination with the increased RT intervals, may trigger torsades de pointes or other types of potentially fatal arrhythmias. To provide a notification of when the patient can resume normal activities, the drug efficacy monitoring unit monitors RT intervals following delivery of the antiarrhythmic drug and to compares the RT intervals against a threshold value representative of the nominal RT intervals for the patient. Once the RT intervals have returned to nominal, an appropriate notification signal is forwarded to the bedside monitor and/or external programmer. This RT interval notification feature may be activated, for example, by having the patient (or physician) manually control the bedside monitor (or external programmer) to forward an activation signal to the implanted device when the patient takes the drug. Thereafter, the monitoring unit specifically monitors RT intervals (along with any other on-going monitoring) and issues the notification signal at eh appropriate time. Alternatively, the monitoring device can be programmed to detect the administration of the drug based on its effects on RT intervals and other cardiac signal features, then generate the notification signal once the RT intervals have returned to nominal.

Thus, FIG. 5 provides as overview of a method for automatically monitoring and verifying antiarrhythmic drug efficacy. Individual features of the patient cardiac signal (such as VER or R-wave width, RT interval, etc.) are compared against stored values representative of the effects on the features caused by the various classes of antiarrhythmic drugs to identify the class of drug taken by the patient and evaluate its efficacy. More specifically, for each class of drug, one or more values are stored representing the effects, if any, drugs within the class have on the shape, duration and relative timing of P-waves, R-waves, T-waves, AERs, and VERs. For AERs and VERs, duration refers to the delay from delivery of a pacing pulse until the resulting evoked response. For P-waves, R-waves, and T-waves, timing refers to the intervals therebetween—specifically the PR interval and RT intervals. Depending upon the specific implementation, the drug effect values either 1) represent qualitative changes or trends in the features caused by the drug (e.g. values specify whether the PR interval is expected to be increased or deceased by a particular class of drugs) or 2) provide a template quantifying the expected resulting features absolutely (e.g. values specify the expected duration of the resulting PR interval in milliseconds) or 3) provide a template quantifying expected changes or trends in features (e.g. 10% shortening of VER duration). If trend-based changes are represented, the antiarrhythmic drug efficacy monitoring unit compares patient cardiac signal features detected before the drug has been administered with corresponding features detected after the drug has been taken to verify that the drug is causing the expected changes in the cardiac signal. If template-based features are instead represented, the analysis unit compares cardiac signal features detected after the drug has been taken with pre-stored templates to verify that the detected features match the stored templates. A combination of both approaches can also be used.

a. Trend-Based Comparison

Figure 6:
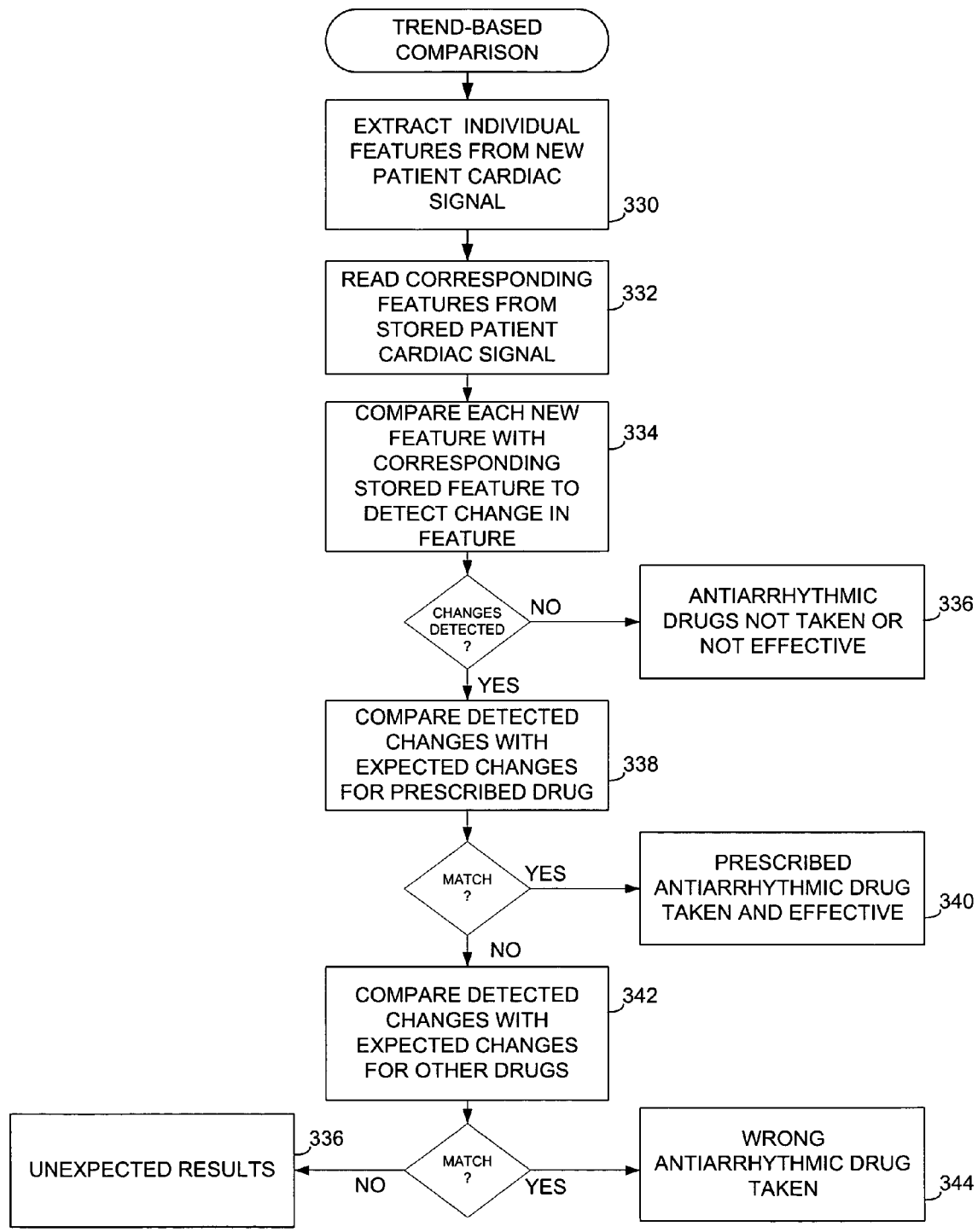
FIG. 6 is a flow chart illustrating a trend-based method for use with the technique of FIG. 5 for evaluating drug efficacy.

For the trend-based approach, the comparison operation (step 308 of FIG. 5) is illustrated in FIG. 6. Initially, at step 330, the analysis unit (unit 152 of FIG. 2) processes new patient cardiac electrical signals to identify the following events: P-waves, R-waves, or AERs and VERs and T-waves, as appropriate for the current pacing mode. Then the analysis unit processes the electrograms of the identified events to derive average values for several predefined features, particularly the duration and slope. Also, average timing intervals are derived for unpaced PR and RT intervals or paced A-R and V-T intervals, again as appropriate for the current pacing mode. Variability in the above timing intervals is also derived. If paced, average durations are detected for AER and VER. The sinus rate is also detected and is used, for example, to normalize the detected values to permit reliable comparison of signal features. Thus, for example, RT intervals can be first normalized based on sinus rate, before being averaged together. Variability, for example of the sinus interval, may be calculated by keeping a history of several preceding intervals in memory and applying any one of a number of well understood calculations, such as that described by the formula:

$$S^2 = \mathrm{SUM}_{P=1\ to\ N}(X_P\_M)^2/(N-1)$$

where S is the variance of a sample, N is the number of intervals sampled, M is the mean of the intervals sampled, $X_P$ represents the Pth of the N samples stored, and variability is defined as S. In the present application, N is preferably constant, with exemplary values being 32, 64 or 100. Because N is known and constant, the variability feature may be defined by the simplified formula:

$$\mathrm{Variability} = \mathrm{SUM}_{P=1\ to\ N}(\mathrm{ABS}\ (X_P\_M)).$$

ABS ( ) defines the absolute value function. Variability may also be defined by other methods, such as those taught in U.S. Pat. No. 5,941,831 "Method for Diagnosing Cardiac Arrhythmias Using Interval Variability" which is included herein by reference. Variability is also preferably normalized for sinus rate. Variability measurements may also be averaged. Averages are preferably based on several hours worth of IEGM signals detected while the patient is asleep.

Also, in general, any quantifiable aspect of the morphology of an electrical cardiac event may potentially be used as a feature for analysis. Routine experimentation may be performed to identify helpful morphological features. For morphology analysis techniques, see U.S. Pat. No. 5,779,645 to Olson, et al. and U.S. Pat. No. 6,516,219 to Street.

The various features to be detected are listed in TABLE II. Note that TABLE II is merely exemplary of a set of cardiac signal features that can be used to verify drug efficacy and, in other implementations, additional or alternative features may instead be used (so long as the features are sufficient to permit each of the classes of drugs to be uniquely identified.) Additional information regarding exemplary sets of features is provided below.

TABLE II

| EVENT | FEATURE | | |
|---|---|---|---|
| | DURATION | VARIABILITY | SLOPE |
| P-WAVE | | N/A | |
| R-WAVE | | N/A | |
| T-WAVE | | N/A | |
| PR (OR A-R) | | | N/A |
| RT (OR V-T) | | | N/A |
| AER | | N/A | |
| AER DELAY | | N/A | N/A |
| VER | | N/A | |
| VER DELAY | | N/A | N/A |
| SINUS INTERVAL | | | |

At step 332, stored average values for the corresponding features are retrieved from memory. The stored values are preferably derived from patient cardiac electrical signals processed before taking the prescribed antiarrhythmic drug. For example, during an office visit in which an antiarrhythmic drug is prescribed, the physician may program the implanted device to record average values for the various features the following night while the patient is asleep, then instruct the patient to begin taking the new antiarrhythmic drug the following day. In any case, at step 334, each average value (derived at step 320) is compared with the corresponding average (retrieved at step 332) to detect significant changes, if any, caused by the prescribed drug. The comparison at step 334 may employ pre-programmed threshold percentages, such as 10% or 20%, to specify the amount of change regarded as "significant". In any case, if no changes are detected at step 334, the analysis unit thereby concludes at step 336 that the prescribed antiarrhythmic drug either was not taken by the patient or was ineffective and an appropriate warning signal is issued to the patient (step 314 of FIG. 5). If significant changes are detected, then the antiarrhythmic drug efficacy monitoring unit compares the detected changes with the stored trend values representative of changes expected to be caused by the prescribed drug, at step 338.

If the changes detected in the patient cardiac electrical signals correctly match the stored trend values, the analysis unit thereby concludes at step 340 that the correct prescribed antiarrhythmic drug had been taken by the patient and is effective and an appropriate confirmation signal is issued to the patient (step 314 of FIG. 5). If the detected changes do not match the stored trend values, then the analysis unit compares the detected changes with stored trend values for all other classes of antiarrhythmic drugs, at step 342. If a match occurs, the analysis unit thereby concludes at step 344 that the wrong antiarrhythmic drug had been taken by the patient. If still no match is found, an appropriate warning signal is issued at step 346 indicating that significant changes were detected in the cardiac electrical signals but the changes do not match those expected for any of the classes of antiarrhythmic drugs.

The comparison of step 338 is performed by accessing one or more stored trend tables listing expected changes in selected features. Based on the information in the trend tables, the analysis unit identifies the particular class of antiarrhythmic drug most likely to have been taken by the patient, assuming the drug is reasonably effective. Note that the analysis unit need not detect or analyze all of the cardiac signal features listed in TABLE II but can instead draw conclusions based on selected combinations (or sub-sets) of features programmed into the unit. For example, increased RT intervals (or V-T intervals), and/or decreased T-wave slope indicate the likely presence of Class 1A or class III drugs. Class 1A is more likely, however, if the above effects are accompanied by a decrease in R-wave slope and/or an increase in R-wave duration. Class IB drugs can be uniquely identified by a decreased RT interval (or V-T interval) combined with minimal changes to other features. Class IC drugs can be uniquely identified based on a combination of decreased P-wave and R-wave slopes (or AER or VER slopes) and/or increased P-wave and R-wave duration (or AER and VER duration) with unchanged T-wave slope and unchanged RT (or V-T) duration. An increased PR interval combined with an increased sinus interval indicate the likely presence of Class II or Class IV drugs. However, a Class II drug is more likely if a decreased variability in sinus interval and PR interval is also observed. Class IV drugs are uniquely identified based a combination of increased PR (or A-R) duration and increased sinus interval, along with minimal changes to other features.

Numerous other sub-sets of features can be designated for uniquely identifying the various classes of drugs. TABLES III–VIII list the expected changes, if any, to each cardiac signal feature of TABLE II for each of the currently recognized classes of antiarrhythmic drugs. For new classes of antiarrhythmic drugs that may be developed, similar tables can be generated by those skilled in the art based on routine drug analysis studies and then particular combinations of features can be selected for uniquely identify any drugs within the new class based on effects on patient cardiac electrical signals. Hence, the invention is not limited for use with the particular classes of antiarrhythmic drugs listed in Tables III–VIII.

TABLE III

CLASS IA

| EVENT | FEATURE | | |
|---|---|---|---|
| | DURATION | VARIATION | SLOPE |
| P-WAVE | INCREASED | N/A | DECREASED |
| R-WAVE | INCREASED | N/A | DECREASED |
| T-WAVE | INCREASED | N/A | DECREASED |
| PR (OR A-R) | INCREASED or DECREASED | NO CHANGE | N/A |
| RT (OR V-T) | INCREASED | N/A | N/A |
| AER | INCREASED | N/A | DECREASED |
| VER | INCREASED | N/A | DECREASED |
| SINUS INTERVAL | NO CHANGE | NO CHANGE | N/A |

TABLE IV

CLASS IB

| EVENT | FEATURE | | |
|---|---|---|---|
| | DURATION | VARIATION | SLOPE |
| P-WAVE | NO CHANGE | N/A | NO CHANGE |
| R-WAVE | NO CHANGE | N/A | NO CHANGE |
| T-WAVE | NO CHANGE | N/A | NO CHANGE |
| PR (OR A-R) | NO CHANGE | NO CHANGE | N/A |
| RT (OR V-T) | DECREASED | N/A | N/A |
| AER | NO CHANGE | N/A | NO CHANGE |
| VER | NO CHANGE | N/A | NO CHANGE |
| SINUS INTERVAL | NO CHANGE | NO CHANGE | N/A |

TABLE V

CLASS IC

| EVENT | FEATURE | | |
|---|---|---|---|
| | DURATION | VARIATION | SLOPE |
| P-WAVE | INCREASED | N/A | DECREASED |
| R-WAVE | INCREASED | N/A | DECREASED |
| T-WAVE | NO CHANGE | N/A | NO CHANGE |
| PR (OR A-R) | INCREASED | NO CHANGE | N/A |
| RT (OR V-T) | NO CHANGE | N/A | N/A |
| AER | INCREASED | N/A | DECREASED |
| VER | INCREASED | N/A | DECREASED |
| SINUS INTERVAL | NO CHANGE | NO CHANGE | N/A |

TABLE VI

CLASS II

| EVENT | FEATURE | | |
|---|---|---|---|
| | DURATION | VARIATION | SLOPE |
| P-WAVE | NO CHANGE | N/A | NO CHANGE |
| R-WAVE | NO CHANGE | N/A | NO CHANGE |
| T-WAVE | NO CHANGE | N/A | NO CHANGE |
| PR (OR A-R) | INCREASED | DECREASED | N/A |
| RT (OR V-T) | NO CHANGE | N/A | N/A |
| AER | NO CHANGE | N/A | NO CHANGE |
| AER DELAY | NO CHANGE | N/A | N/A |
| VER | NO CHANGE | N/A | NO CHANGE |
| VER DELAY | NO CHANGE | N/A | N/A |
| SINUS INTERVAL | INCREASED | DECREASED | N/A |

TABLE VII

CLASS III

| EVENT | FEATURE | | |
|---|---|---|---|
| | DURATION | VARIATION | SLOPE |
| P-WAVE | NO CHANGE | N/A | NO CHANGE |
| R-WAVE | NO CHANGE | N/A | NO CHANGE |
| T-WAVE | INCREASED | N/A | DECREASED |
| PR (OR A-R) | NO CHANGE | NO CHANGE | N/A |
| RT (OR V-T) | INCREASED | N/A | N/A |
| AER | NO CHANGE | N/A | NO CHANGE |
| VER | NO CHANGE | N/A | NO CHANGE |
| SINUS INTERVAL | INCREASED | NO CHANGE | N/A |

TABLE VIII

CLASS IV

| EVENT | FEATURE | | |
|---|---|---|---|
| | DURATION | VARIATION | SLOPE |
| P-WAVE | NO CHANGE | N/A | NO CHANGE |
| R-WAVE | NO CHANGE | N/A | NO CHANGE |
| T-WAVE | NO CHANGE | N/A | NO CHANGE |
| PR (OR A-R) | INCREASED | NO CHANGE | N/A |
| RT (OR V-T) | NO CHANGE | N/A | N/A |
| AER | NO CHANGE | N/A | NO CHANGE |
| AER DELAY | N/A | N/A | N/A |
| VER | NO CHANGE | N/A | NO CHANGE |
| VER DELAY | N/A | N/A | N/A |
| SINUS INTERVAL | INCREASED | NO CHANGE | N/A |

Figure 7:
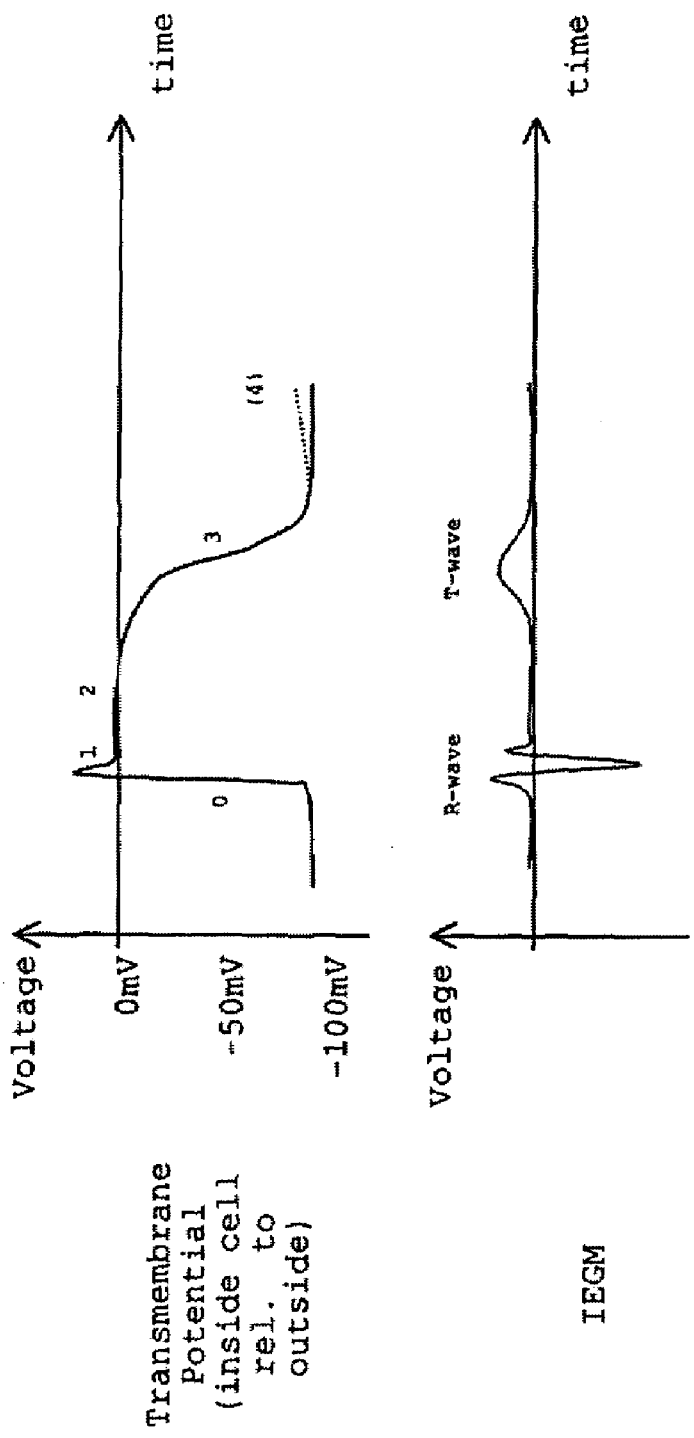
FIG. 7 illustrates an exemplary cardiac signal representative of the effects of Class IC antiarrhythmic drugs.

The values of TABLES III–VIII have been derived based on well understood effects on cardiac electrical signals caused by the various classes of antiarrhythmic drugs. FIG. 7 illustrates the effects of Class IC drugs on the various phases of a cardiac signal. More specifically, FIG. 7 illustrates the action potential for a single ventricular myocardial cell along with the wideband IEGM signal detected using a bipolar sensing electrode positioned close to the cell. The various phases shown in FIG. 7 are as follows:

| | |
|---|---|
| Phase 0 | transient inward Na$^+$ current ($I_{Na}$) |
| Phase 1 | inactivation of $I_{Na}$ transient outward K$^+$ current ($I_{qr}$) |
| Phase 2 | membrane conductance reduced, slow inward Ca$^{2+}$ channel open ($I_{si}$) |
| Phase 3 | outward K~ current ($I_{X1}$) |
| Phase 3 | "pacemaker current" (nodal/Purkinje cells) inward Na$^+$ ($I_f$) |

Background currents: inward Na$^+$ and Ca$^{2+}$ ($I_{K1}$); tends to depolarize outward K+ ($I_{K1}$); tends to repolarize.

Class IC drugs reduce the maximum positive slope and width of the AER and VER as well as P-waves and R-waves, because Class IC drugs block sodium channels, thus slowing Phase 0 depolarization of myocardial tissue as shown in FIG. 7. This in turn reduces the propagation velocity of depolarization, causing the propagating wave of depolarization to remain in the vicinity of the sensing electrode for a longer time, which in turn produces a longer-lasting P-wave, R-wave, AER or VER. Variables other than propagation velocity (such as propagation direction) are less likely to affect features of the AER and VER than they are to affect features of P-waves and R-waves and so AER and VER features are more trustworthy indicators.

As another example, Class IA and III drugs increase RT intervals. The RT interval is increased because these drugs inhibit potassium channels and thus slow and/or delay the process of repolarization, i.e. Phase 3 of the action potential. It is this feature of the action potential produced by the ventricular myocardial cells in the vicinity of the sensing electrode which gives rise to the T-wave detected in the IEGM. Delay of Phase 3 repolarization has the primary effect of lengthening the RT interval. Similar reasoning applies to the V-pulse to T-wave interval in a ventricular paced cycle. The maximum slope of the T-wave is also reduced by Class IA and III drugs. Reduction of the rate of Phase 3 depolarization has the primary effect of reducing the maximum slope of the T-wave.

As yet another example, Class IV drugs affect PR interval by inhibiting the calcium channel, which is responsible for Phase 0 depolarization in the "slow response" cells of the AV node instead of sodium channels. By slowing Phase 0 depolarization, Class IV drugs decrease the propagation velocity through the AV node and thereby increase PR interval. Similar reasoning applies to the A-pulse to R-wave interval in an atrial paced cycle.

b. Template-Based Comparison

Figure 8:
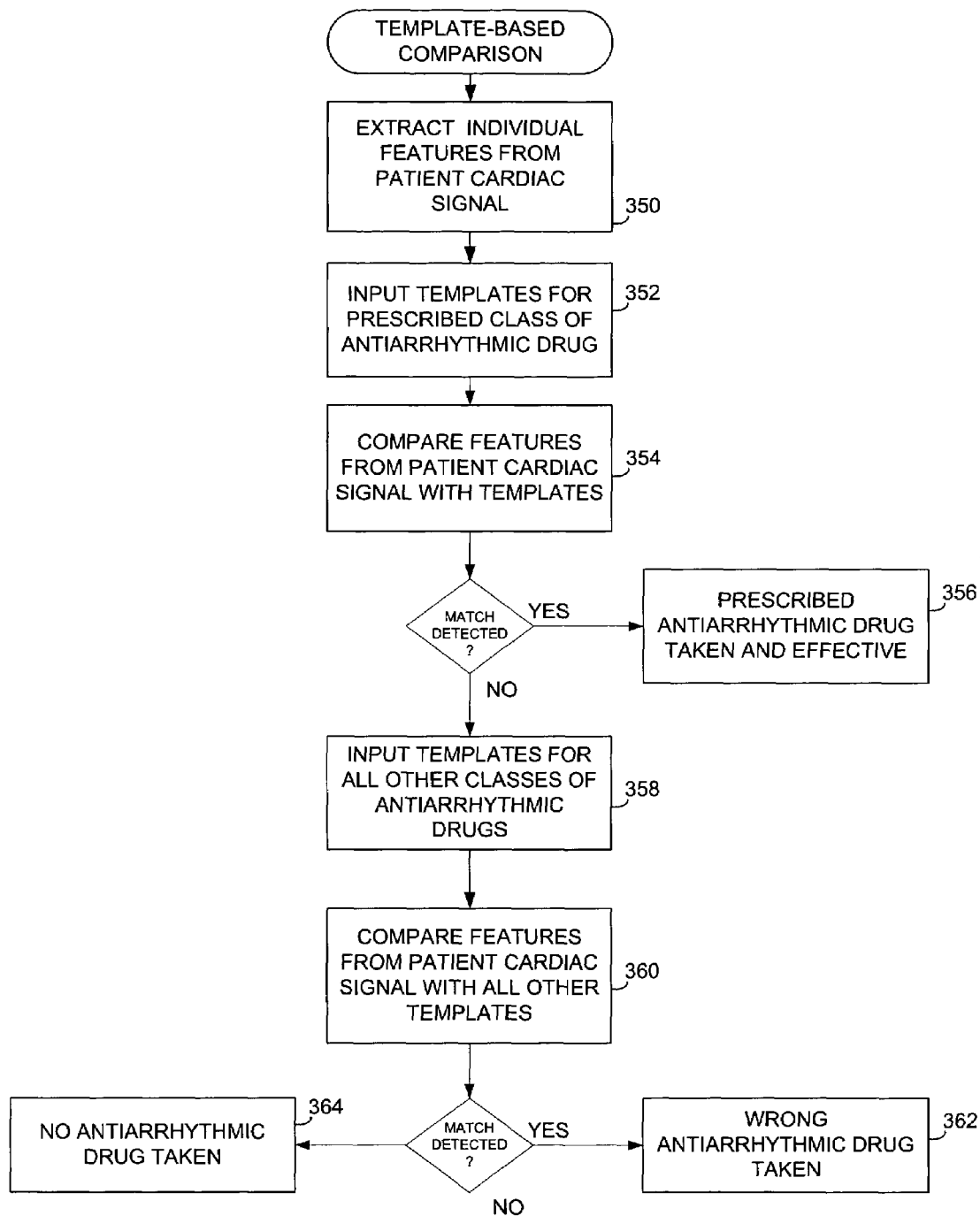
FIG. 8 is a flow chart illustrating a template-based method for use with the technique of FIG. 5 for evaluating drug efficacy.
Figure 9:
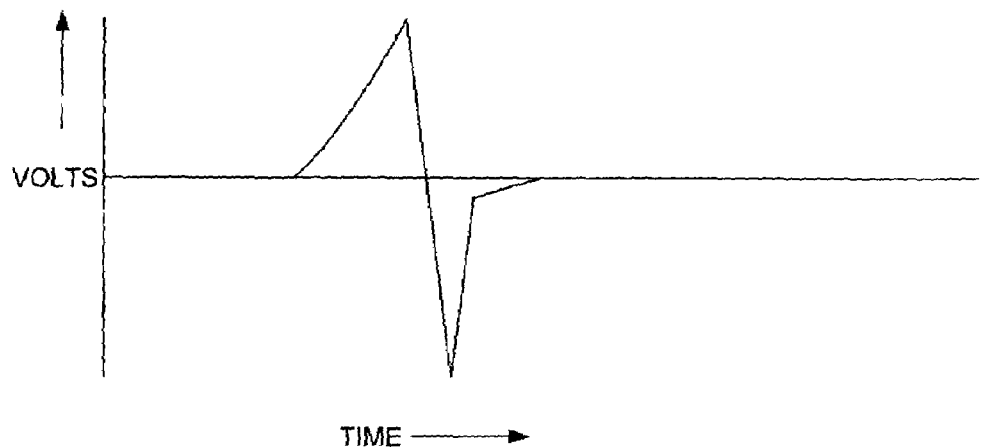
FIG. 9 illustrates an exemplary average R-wave shape derived from a patient cardiac signal for use with the template-based method of FIG. 8.
Figure 10:
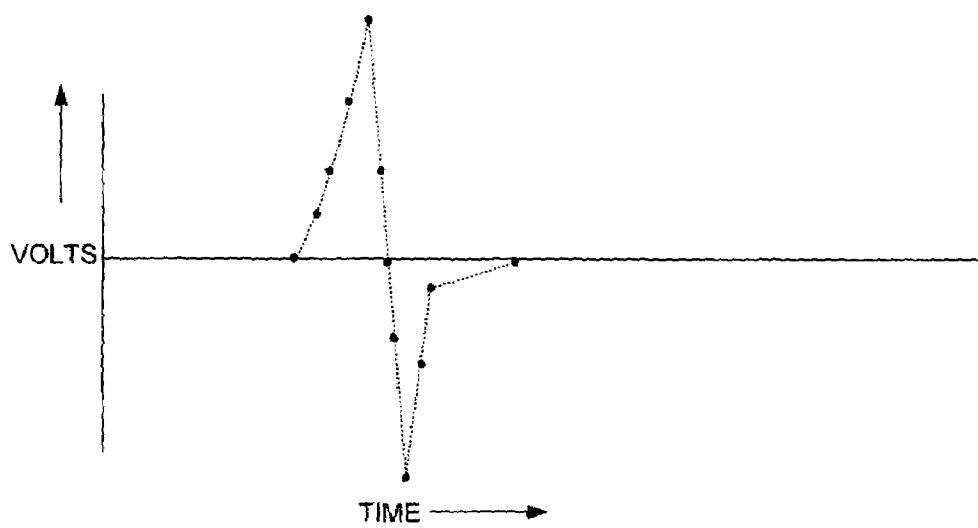
FIG. 10 illustrates an exemplary expected R-wave shape representative of the effects of Class IA antiarrhythmic drugs for use with the template-based method of FIG. 8.

For the template-based approach, the comparison operation performed by the antiarrhythmic drug efficacy monitoring unit (step 308 of FIG. 5) is illustrated in FIG. 8. At step 350, the analysis unit processes new patient cardiac electrical signals to derive average values for the various signal features discussed above, such as duration and slope, as well as to derive an average shape for the signal feature. In other words, a table similar to that of TABLE II is generated, but additionally providing average detected shapes for the P-wave, R-wave, T-wave, AER and VER found within the patient cardiac electrical signals. FIG. 9 illustrates an exemplary average shape for detected patient R-waves. As with the trend-based approach, averages are preferably based on several hours worth of IEGM signals detected while the patient is asleep and adjustment are made based on average sinus rate. At step 352, pre-stored templates are retrieved from memory, which are representative of the shapes and attribute values expected to be present in the patient cardiac electrical signals as a result of use of the particular class of antiarrhythmic drug prescribed to the patient. For example, whereas R-waves within patients taking a Class IA drug may exhibit one shape (on the average), patients taking a Class IV drug may have a completely different average R-wave shape. Expected features, such as expected P-wave shapes, R-wave shapes, etc., are stored, for example, using individual amplitude values as a function of time or using any other appropriate signal shape representation, such as a polynomial representation. FIG. 10 illustrates an exemplary R-wave template shape expected to result from use of a Class IA antiarrhythmic drug stored using individual amplitude values. Expected attribute values, such as P-wave amplitude, PR interval duration, T-wave slope, etc., are represented by ranges of values, typically in milliseconds or millivolts.

The pre-stored template values are preferably derived from studies based on entire populations of patients receiving antiarrhythmic drugs. For example, IEGM signals are recorded from thousands of patients taking Class IA drugs then averaged to derive the various expected template values for Class IA. Likewise, IEGM signals are recorded from thousands of patients taking each of the other classes of drugs and averaged to derive template values for those classes of drugs as well. In other words, a set of tables similar to TABLES III–VIII are generated, but providing expected attribute values rather than merely trend values and additionally providing average shapes for the P-wave, R-wave, T-wave, AER and VER found within the patient cardiac electrical signals. Preferably, IEGM signals from patients from different age groups and genders are averaged separately to provide more reliable templates for use with individual patients. Then, for any particular patient, the device implanted within the patient is programmed using only template values for the same gender and age group. Templates may be further differentiated based on other patient characteristics such as height, weight, and medical history. Ideally, the templates stored for use with a particular patient are based on averaged IEGM signals derived only from similar patients. For this reason, specific template values are not provided herein.

In any case, at step 354, each average value or shape (derived at step 350) is compared with the corresponding template value or shape (retrieved at step 352) to detect a match. If the patient cardiac signal features correctly match the stored template, the analysis unit thereby concludes at step 356 that the correct prescribed antiarrhythmic drug had been taken by the patient and was effective and an appropriate confirmation signal is issued to the patient (step 314 of FIG. 5). If not, processing proceeds to step 358 wherein templates for the other classes of antiarrhythmic drugs are retrieved and compared with the detected signal features at step 360 to detected a possible match. For example, the detected R-wave shape of FIG. 9 may be compared at step 354 with the template R-wave shape of FIG. 10. Since the two shapes are fairly different, the analysis unit would not detect a match, and steps 358 and 360 would then be performed to compare the R-wave shape of FIG. 9 with R-wave template shapes for the other classes of drugs. If a match is detected at step 360, the analysis unit thereby concludes at step 362 that the wrong class of antiarrhythmic drug had been taken by the patient and an appropriate warning signal is issued to the patient (step 314 of FIG. 5). If still no match is found, an appropriate warning signal is issued at step 364 indicating that the patient cardiac electrical signals do not match expected characteristics of any of the classes of antiarrhythmic drugs.

Insofar as the comparisons are concerned, the comparison of feature shapes (such as actual R-wave shape vs. expected R-wave shape) may be performed using a least squared error technique providing a single value representative of the similarity of the two shapes that can then be compared with a pre-determined threshold value to thereby evaluate the match. Comparison of initial values (such as actual PR interval vs. expected PR interval) may be performed by determining a percent difference between the values then comparing the percent differences with a pre-programmed threshold percentage to evaluate the match. Moreover, a entire set of comparison values representative of the differences between all of the features of the patient signal and all of the template values, can be combined to yield a single "metric" value for comparing against a single threshold metric to evaluate the match. As can be appreciated, a wide variety of comparison techniques may be employed, consistent with the general principles of the invention.

What have been described thus far are various techniques for verifying prescription drug compliance and evaluating antiarrhythmic drug efficacy and for issuing appropriate warning signals, if prescribed drugs are not being taken or are ineffective. Although described with respect to the embodiment wherein the implanted device performs the drug efficacy analysis, the external programmer or bedside monitor can instead be programmed to perform this function based on patient cardiac electrical signals forward from the implanted device. In the following, techniques are described for using additionally controlling the implanted device to either control drug pumps to adjust the delivery of antiarrhythmic drugs in view of drug inefficacy or to control pacing parameters to compensate for drug inefficacy. Many aspects of the following techniques are similar to techniques already described and only pertinent differences will be described in detail.

Automatic Control of Drug Pumps

Figure 11:
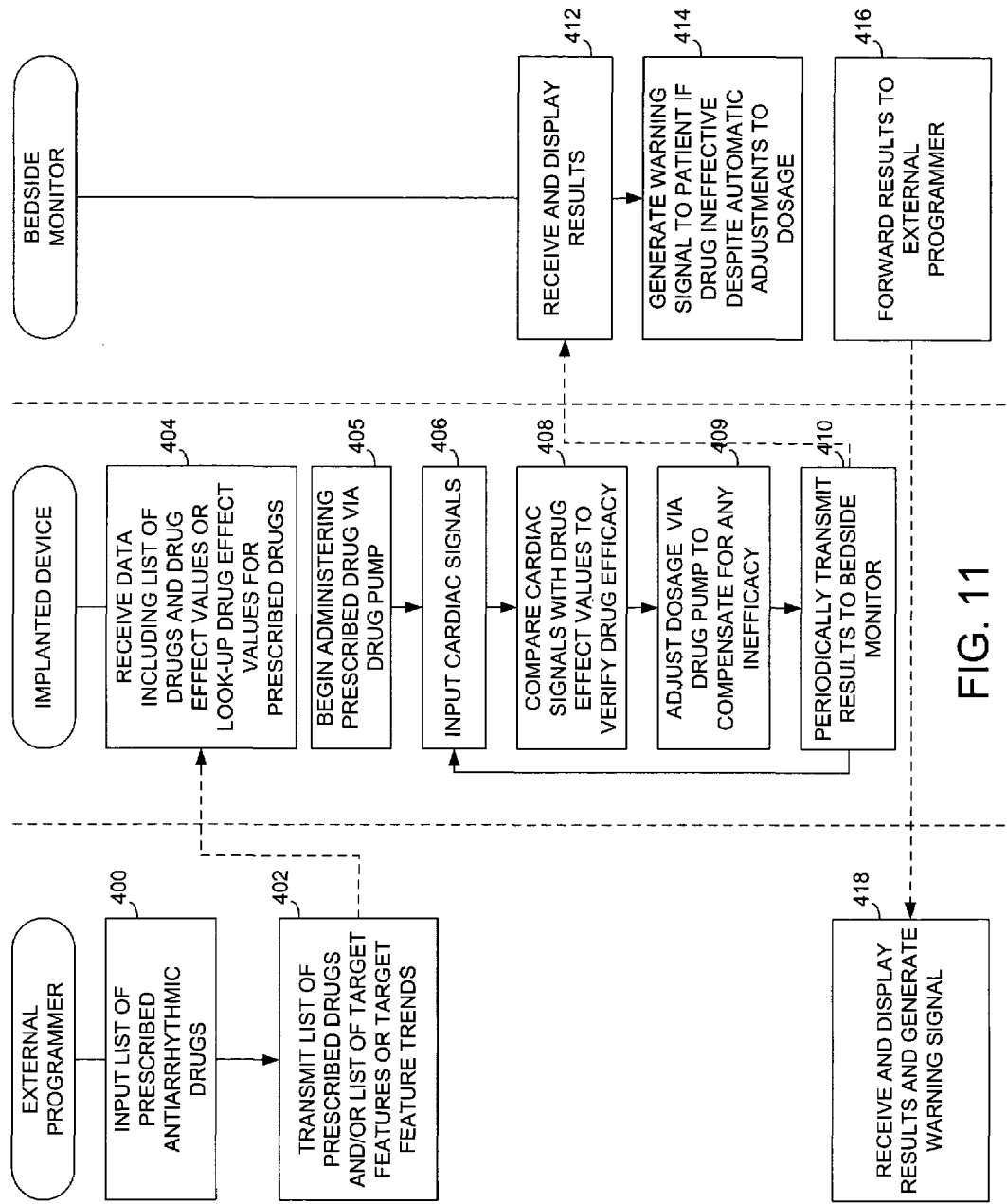
FIG. 11 is a flow chart illustrating, at a high level, a second exemplary method for monitoring drug efficacy, which employs the implantable device and drug pumps of FIG. 9, the external programmer of FIG. 3 and a bedside monitoring unit of FIG. 4 and wherein drug pumps are automatically controlled to adjust drug dosage to maintain adequate drug efficacy.

The method of FIG. 11 operates to evaluate the efficacy of antiarrhythmic drugs delivered to a patient via a drug pump and to automatically adjust the dosage of the drug delivered by the drug pump to maintain adequate drug efficacy. Warning signals are generated if, despite adjustments to the dosage delivered by the drug pump, adequate drug efficacy is still not achieved. At steps 400 and 402, a list of antiarrhythmic drugs provided within the drug pump are input via the external programmer and transmitted to the implanted device. Alternatively, or additionally, lists of target features or target feature trends may be transmitted. Also, an initial prescribed dosage is entered and transmitted. The analysis unit of the implanted device, at step 404, accesses a drug effect table to retrieve values representative of the effects of the listed drugs on patient cardiac electrical signals. Alternatively, the drug effect values are received from the external programmer. Also, as before, either trend-based or template-based values may be used. At step 405, the drug pump control unit (unit 158 of FIG. 2) controls the drug pump to begin delivering the pre-programmed dosage of the antiarrhythmic drug.

Patient cardiac electrical signals are detected at step 406 and compared with pre-stored drug effect values at step 408 to verify that the patient cardiac electrical signals exhibit the effects expected for the drugs delivered by the drug pumps. Comparison at step 408 is preferably delayed an appropriate amount of time to permit the drugs to take affect, typically at least twenty-four hours. In any case, if the patient cardiac electrical signals do not exhibit the expected effects, the drug pump control unit adjusts the dosage at step 409 in an attempt to compensate. If the antiarrhythmic drugs are not achieving sufficient efficacy, the dosage is increased. If antiarrhythmic drugs are achieving greater efficacy than expected, the dosage is decreased. Diagnostic information is periodically transmitted at step 410 to the bedside monitor indicative of the efficacy of the drugs and any changes in dosage made by the drug pump control unit. Warning signals are generated at step 414 if the drug is still ineffective despite a series of adjustments to the dosage. Warning signals and diagnostic information also forwarded to the programmer at step 416 for display at step 418.

In this manner, the drug pump is automatically controlled to in an attempt to compensate for any inefficacy in the antiarrhythmic drugs delivered by the drug pump. Alternatively, rather than using the drug pump as the sole delivery system for the prescribed drug, the drug pump can instead be activated only when needed to increase drug dosage to compensate for a detected lack of efficacy in drugs ingested by the patient or perhaps to deliver a standard dosage of the drug if the patient has forgotten to take the drug. Also, although described with respect to the embodiment wherein the implanted device controls adjustments to the drug pump, the external programmer or bedside monitor can instead be programmed to perform this function based on patient cardiac electrical signals or other diagnostic information forward from the implanted device.

Automatic Adjustment of Pacing and Defibrillation Control Parameters

Figure 12:
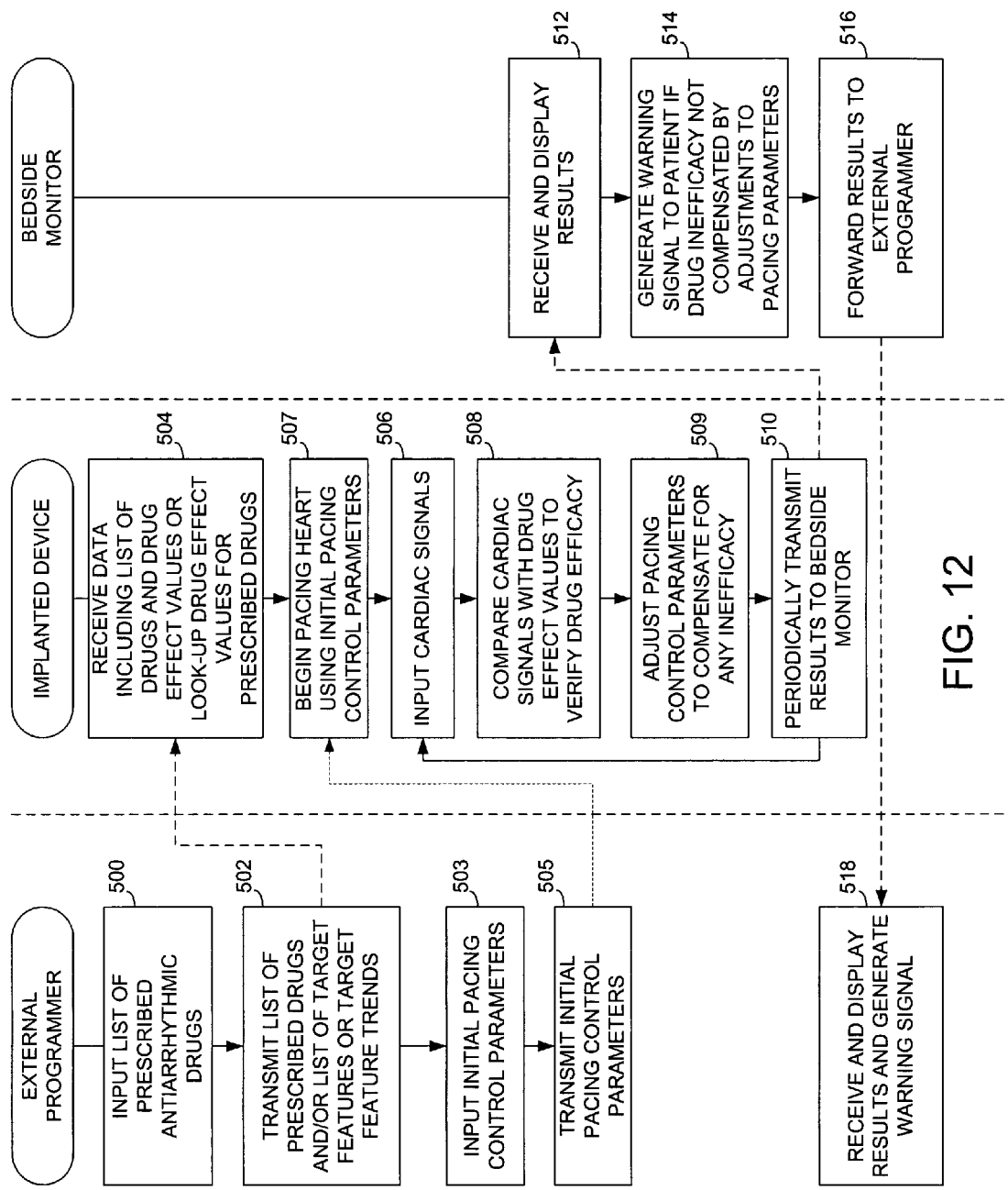
FIG. 12 is a flow chart illustrating, at a high level, a third exemplary method for automatically monitoring drug efficacy, which employs the implantable device of FIG. 2, the external programmer of FIG. 3 and a bedside monitoring unit of FIG. 4 and wherein pacing control parameters are automatically controlled to adjust for any drug inefficacy.

The method of FIG. 12 operates to evaluate the efficacy of antiarrhythmic drugs prescribed to a patient and to automatically adjust pacing or defibrillation control parameters to compensate for any drug inefficacy. At steps 500 and 502, the list of antiarrhythmic drugs prescribed the patient are input via the external programmer and transmitted to the implanted device. Alternatively, or additionally, lists of target features or target feature trends may be transmitted. At steps 503 and 505, initial pacing or defibrillation control parameters, such as overdrive pacing control parameters, are also input via the external programmer and transmitted to the implanted device. The analysis unit of the implanted device, at step 504, accesses either a either trend-based or template-based drug effect table to retrieve values representative of the effects of the prescribed drugs on patient cardiac electrical signals. At step 507, the implanted device begins pacing the heart, if needed, in accordance with the initial control parameters. The initial control parameters, for example, may provide for generally non-aggressive overdrive pacing.

Patient cardiac electrical signals are detected beginning at step 506 and compared with the pre-stored drug effect values at step 508 to verify that the patient cardiac electrical signals exhibit the effects expected for the prescribed drugs. If the patient cardiac electrical signals do not exhibit the expected effects, the control parameter adjustment unit adjusts the control parameters at step 509 in an attempt to compensate. Adjustments may be based on the particular drug prescribed to the patient. For example, for patients receiving antitachycardia drugs, if the drugs are not achieving sufficient efficacy, overdrive pacing control parameters may be adjusted to make the overdrive pacing more aggressive. If drugs achieve greater efficacy than expected, overdrive pacing may be controlled to be less aggressive or may be discontinued completely. Also, adjustments may be based on particular features of the cardiac signal expected to be effected by the prescribed drug. For example, for patients receiving drugs intended to elevate sinus rate, if the drug does not in fact elevate the sinus rate, base rate control parameters may be adjusted to automatically elevate the base rate via pacing. Automatic adjustments to the control parameters are permitted only within predetermined ranges of control parameter values and only for particular control parameters specified by the physician. Diagnostic information is periodically transmitted at step 510 to the bedside monitor indicative of the efficacy of the drugs and any changes in control parameters made by the antiarrhythmic drug efficacy monitoring unit. Warning signals are generated at step 514 if further adjustments to the control parameters are not permissible (e.g. the control parameters have already been adjusted to maximum or minimum permissible values) or are otherwise not expected to adequately compensate for the drug inefficacy. Warning signals and diagnostic information also forwarded to the programmer at step 516 for display at step 518.

In this manner, pacing or defibrillation control parameters are automatically adjusted in an attempt to compensate for any unexpected increase or decrease in the efficacy of antiarrhythmic drugs prescribed to the patient. A wide variety of pacing and defibrillation control parameters may be selected by the physician for automatic adjustment including parameters specifying the pacing mode of the device, such as whether the device is to operate in a dual-chambered mode or a single-chambered mode, the type of response to be performed if a pacemaker mediated tachycardia (PMT) or a pre-ventricular contraction (PVC) is detected, and whether any rate responsive sensors of the device are to be turned on or off (such as minute ventilation sensors). Other control parameters that may be automatically adjusted include the pacing base rate, maximum tracking rate, sensor rate, sensor slope and sensor threshold of the implanted device, overdrive pacing control parameters and defibrillation control parameters.

Insofar as overdrive pacing is concerned, the control parameters may specify 1) the overdrive pacing response function or response "slope"; 2) the number of overdrive events; 3) the recovery rate; 4) the base rate; 5) the rest rate; and 6) the circadian base rate. Briefly, the overdrive pacing response function specifies an overdrive pacing rate to be applied when overdrive pacing is triggered with the overdrive pacing rate dependent upon the detected heart rate. Overdrive pacing is triggered, for example, upon the detection of two consecutive intrinsic heart beats. The number of overdrive events specifies the number of consecutive beats to be paced following triggering of overdrive pacing. The recovery rate specifies a rate decrement by which the pacing rate is to be decreased after the number of overdrive events have been paced. The base rate specifies a standard non-overdrive pacing rate for use while the patient is awake. Further information regarding the automatic adjustment of pacing control parameters may be found in: U.S. patent application Ser. No. 10/043,781, "Method And Apparatus For Dynamically Adjusting A Non-Linear Overdrive Pacing Response Function", filed Jan. 9, 2002; and U.S. patent application Ser. No. 10/043,472, "Method and Apparatus for Dynamically Adjusting Overdrive Pacing Parameters", filed Jan. 9, 2002, each of which is assigned to the assignee of rights to the present application and is incorporated by reference herein. In particular, automatic control parameter adjustment techniques described in the referenced patents may be used in conjunction with the techniques of the present invention, where consistent.

Insofar as defibrillation control parameters are concerned, the control parameters may specify the shape and strength of cardioversion and defibrillation shocks, the specific circumstances under which the shocking capacitors should be pre-charged, and the specific circumstances under which cardioversion and defibrillation shocks should be delivered. Then, for example, if anti-VT drugs are found to be ineffective, parameters specifying the circumstances under which a shock is delivered may be automatically adjusted to provide for aggressive shock therapy. On the other hand, if the anti-VT drugs are found to be generally effective, the parameters may be adjusted so as to provide for less aggressive shock therapy. As another example, if anti-VT drugs are found to be ineffective, defibrillation capacitors can be automatically pre-charged whenever RT intervals increase beyond a predetermined threshold. If the anti-VT drugs are instead generally effective, the capacitors are not pre-charged until an episode of VT is actually detected.

Also, although described with respect to the embodiment wherein the implanted device controls adjustments to the pacing control parameters, the external programmer or bedside monitor can instead be programmed to perform this function based on patient cardiac electrical signals or other diagnostic information forward from the implanted device.

The various functional components of the exemplary system may be implemented using any appropriate technology including, for example, microprocessors running software programs or application specific integrated circuits (ASICs) executing hard-wired logic operations. Although described with respect to a pacemakers and ICDs used in conjunction with an external programmer, aspects of the invention are applicable to other systems, such as systems employing other implantable cardiac stimulation devices or systems employing other types of external interfaces for use with the implantable device. The exemplary embodiments of the invention described herein are merely illustrative of the invention and should not be construed as limiting the scope of the invention.

What is claimed is:

1. A method comprising:
   administering an antiarrhythmic drug to a patient;
   receiving patient cardiac electrical signals via an implantable cardiac stimulation device implanted in the patient;
   analyzing the patient cardiac electrical signals to detect the effects, if any, on the cardiac electrical signals caused by the antiarrhythmic drug; and
   automatically controlling operation of the implantable cardiac stimulation device based on results of the analysis of the patient cardiac electrical signals;
   wherein analyzing the patient cardiac electrical signals comprises determining the most likely class of antiarrhythmic drugs, taken by the patient.

2. The method of claim 1 wherein analyzing the patient cardiac electrical signals comprises analyzing features of events within the signals including one or more of event duration, event slope, time between events, and event variability.

3. The method of claim 1 wherein controlling operation of the implantable cardiac stimulation device comprises outputting a warning signal if the efficacy of the antiarrhythmic drugs falls below a predetermined threshold.

4. The method of claim 1 further comprising inputting a value identifying an antiarrhythmic drug prescribed to the patient and its class and wherein controlling operation of the implantable cardiac stimulation device includes the step of outputting a warning signal if the class of the prescribed drug does not match the class of antiarrhythmic drugs found to have been taken by the patient.

5. The method of claim 1 wherein the implantable cardiac stimulation device includes a drug pump for delivering antiarrhythmic drugs to the patient and wherein controlling operation of the implantable cardiac stimulation device comprises adjusting a dosage of antiarrhythmic drugs delivered by the drug pump based on the results of the analysis of the patient cardiac electrical signals.

6. The method of claim 1 wherein the implantable cardiac stimulation device is capable of performing cardiac pacing and wherein controlling operation of the implantable cardiac stimulation device comprises controlling cardiac pacing based on the results of the analysis of the patient cardiac electrical signals.

7. The method of claim 6 wherein the implantable cardiac stimulation device is capable of performing dynamic overdrive pacing and wherein controlling cardiac pacing comprises controlling an aggressiveness of the overdrive pacing based on the results of the analysis of the patient cardiac electrical signals.

8. The method of claim 1 wherein the implantable cardiac stimulation device is capable of performing defibrillation functions and wherein controlling operation of the implantable cardiac stimulation device comprises controlling defibrillation functions based on the results of the analysis of the patient cardiac electrical signals.

9. The method of claim of 1 wherein the implantable cardiac stimulation device includes a sensor for sensing a physiological parameter affected by anti-arrhythmic drugs and further comprising:
  inputting physiological signals from The sensor; and
  analyzing the physiological signals to corroborate the results of the analysis of the patient cardiac electrical signals.

10. The method of claim 1 wherein analyzing the patient cardiac electrical signals comprises:
  inputting values representative of expected changes to features of cardiac electrical signals caused by antiarrhythmic drugs; and
  comparing features of patient cardiac electrical signals detected after administration of an antiarrhythmic drug with corresponding features of cardiac electrical signals detected before administration of the drug to verify that the expected changes occurred.

11. The method of claim 1 wherein analyzing the patient cardiac electrical signals comprises:
  inputting templates representative of the expected quantitative features of cardiac electrical signals as affected by antiarrhythmic drugs; and
  comparing portions of the patient cardiac electrical signals with the templates to detect the effects, if any, on the cardiac electrical signals caused by antiarrhythmic drugs.

12. The method of claim 1 wherein analyzing the patient cardiac electrical signals comprises:
  inputting templates representative of expected qualitative changes to features of cardiac electrical signals caused by antiarrhythmic drugs; and
  comparing portions of the patient cardiac electrical signals with the templates to detect the effects, if any, on the cardiac electrical signals caused by antiarrhythmic drugs.

13. The method of claim 1 wherein analyzing the patient cardiac electrical signals is performed using only patient cardiac electrical signals detected at substantially the same time of day.

14. The method of claim 1 wherein analyzing the patient cardiac electrical signals cardiac is performed using only averaged patient cardiac electrical signals.

15. The method of claim 1 wherein analyzing the patient cardiac electrical signals to detect the effects, if any, on the cardiac electrical signals caused by antiarrhythmic drugs includes the step of tracking RT intervals affected by antiarrhythmic drugs.

16. A method comprising:
  administering an antiarrhythmic drug to a patient;
  receiving patient cardiac electrical signals via an implantable cardiac stimulation device implanted in the patient;
  analyzing the patient cardiac electrical signals to detect the effects, if any, on the cardiac electrical signals caused by the antiarrhythmic drug; and
  automatically controlling operation of the implantable cardiac stimulation device based on results of the analysis of the patient cardiac electrical signals;
  wherein analyzing the patient cardiac electrical signals to detect the effects, if any, on the cardiac electrical signals caused by antiarrhythmic drugs includes the step of tracking RT intervals affected by antiarrhythmic drugs;
  for use with patients receiving Class III antiarrhythmic drugs wherein controlling operation of the implantable cardiac stimulation device comprises generating a notification signal when RT intervals have returned to a nominal state following patient receipt of the Class III antiarrhythmic drugs.

17. In an implantable cardiac stimulation device for implant within a patient, a system comprising:
  means for administering antiarrhythmic drugs to the patient;
  means for receiving patient cardiac electrical signals;
  means for analyzing the patient cardiac electrical signals to detect the effects, if any, on the cardiac electrical signals caused by antiarrhythmic drugs; and
  means for controlling operation of the implantable cardiac stimulation device based on the results of the analysis of the patient cardiac electrical signals;
  wherein the means for analyzing the patient cardiac electrical signals comprises determining the most likely class of antiarrhythmic drugs, taken by patient.

18. A method comprising:
  prescribing at least one specific antiarrhythmic drug to a patient;
  receiving patient cardiac electrical signals via an implantable cardiac stimulation device implanted in the patient;
  analyzing the patient cardiac electrical signals to monitor for a particular result expected to result from the at least one specific antiarrhythmic drug; and
  generating a warning signal if the particular result is not detected;
  wherein analyzing the patient cardiac electrical signals comprises determining the most likely class of antiarrhythmic drugs, taken by the patient.

* * * * *